(12) United States Patent
Ponmudi et al.

(10) Patent No.: US 12,059,179 B2
(45) Date of Patent: Aug. 13, 2024

(54) EXPANDABLE SPINAL FIXATION SYSTEM

(71) Applicant: GLOBUS MEDICAL, INC., Audubon, PA (US)

(72) Inventors: Varun Ponmudi, Scotch Plains, NJ (US); Jason Zappacosta, Philadelphia, PA (US); Jonathan Perloff, Slatington, PA (US)

(73) Assignee: Globus Medical, Inc., Audubon, PA (US)

(*) Notice: Subject to any disclaimer, the term of this patent is extended or adjusted under 35 U.S.C. 154(b) by 253 days.

(21) Appl. No.: 17/675,347

(22) Filed: Feb. 18, 2022

(65) Prior Publication Data

US 2022/0168023 A1    Jun. 2, 2022

Related U.S. Application Data

(63) Continuation of application No. 16/728,246, filed on Dec. 27, 2019, now Pat. No. 11,350,972, which is a continuation of application No. 15/960,614, filed on Apr. 24, 2018, now Pat. No. 10,548,647, which is a continuation of application No. 15/072,664, filed on Mar. 17, 2016, now Pat. No. 9,974,575, which is a continuation-in-part of application No. 15/012,992, filed on Feb. 2, 2016, now Pat. No. 9,622,793.

(51) Int. Cl.
*A61B 17/70*   (2006.01)
*A61B 17/68*   (2006.01)

(52) U.S. Cl.
CPC ...... *A61B 17/7068* (2013.01); *A61B 17/7076* (2013.01); *A61B 2017/681* (2013.01)

(58) Field of Classification Search
CPC ............ A61B 17/7062; A61B 17/7065; A61B 17/7067–7068
See application file for complete search history.

(56) References Cited

U.S. PATENT DOCUMENTS

| | | | |
|---|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Eduardo C Robert
*Assistant Examiner* — Michelle C Eckman

(57) ABSTRACT

Expandable spinal fixation assemblies, systems, and methods thereof. An expandable spinal fixation system may include expandable barrel assembly including an upper barrel half and a lower barrel half and a fixed barrel assembly. The fixed barrel assembly is insertable between the upper barrel half and the lower barrel half such that the fixed barrel assembly is clamped between the upper barrel half and the lower barrel half. Each of the expandable barrel assembly and the fixed barrel assembly includes fixation plates adapted to secure spinous processes to the fixation system.

17 Claims, 25 Drawing Sheets

(56) References Cited

U.S. PATENT DOCUMENTS

| | | |
|---|---|---|
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,114,132 B2 | 2/2012 | Lyons et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,206,420 B2 | 6/2012 | Patel et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,005,248 B2 | 4/2015 | Taber et al. |
| 9,028,550 B2 | 5/2015 | Shulock et al. |
| 9,066,760 B2 | 6/2015 | Taber et al. |
| 9,358,125 B2 | 6/2016 | Jimenez et al. |
| 9,532,883 B2 | 1/2017 | McLuen et al. |
| 9,622,878 B2 | 4/2017 | Grotz |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0312741 A1* | 12/2008 | Lee ............... A61B 17/7068 606/90 |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |

(56) References Cited

U.S. PATENT DOCUMENTS

| | | |
|---|---|---|
| 2009/0299478 A1 | 12/2009 | Carls et al. |
| 2009/0312763 A1 | 12/2009 | McCormack |
| 2010/0036419 A1* | 2/2010 | Patel ............... A61B 17/7062 606/279 |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0106190 A1* | 4/2010 | Linares ............ A61B 17/7067 606/249 |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0144692 A1* | 6/2011 | Saladin ............. A61B 17/7047 606/249 |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0221050 A1* | 8/2012 | Ingalhalikar ....... A61B 17/7068 606/248 |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0012996 A1* | 1/2013 | Zamani ............. A61B 17/7068 606/279 |
| 2013/0023993 A1 | 1/2013 | Weiman |
| 2013/0023994 A1 | 1/2013 | Glerum |
| 2013/0072979 A1 | 3/2013 | Butler et al. |
| 2013/0158663 A1 | 6/2013 | Miller et al. |
| 2013/0158669 A1 | 6/2013 | Sungarian et al. |
| 2013/0184754 A1* | 7/2013 | Taber ............... A61B 17/7061 606/279 |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2013/0296940 A1 | 11/2013 | Northcutt et al. |
| 2013/0325065 A1 | 12/2013 | Malandain et al. |
| 2014/0067071 A1 | 3/2014 | Neiman et al. |
| 2014/0088714 A1 | 3/2014 | Miller et al. |
| 2014/0163683 A1 | 6/2014 | Seifert et al. |
| 2014/0188170 A1* | 7/2014 | Zappacosta ........ A61B 17/7062 606/249 |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 2446843 A2 | 8/2009 |
| EP | 3111896 A1 | 1/2017 |
| FR | 2794968 A1 | 12/2000 |
| JP | 2000-513263 A | 10/2000 |
| JP | 2012-500057 A | 1/2012 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

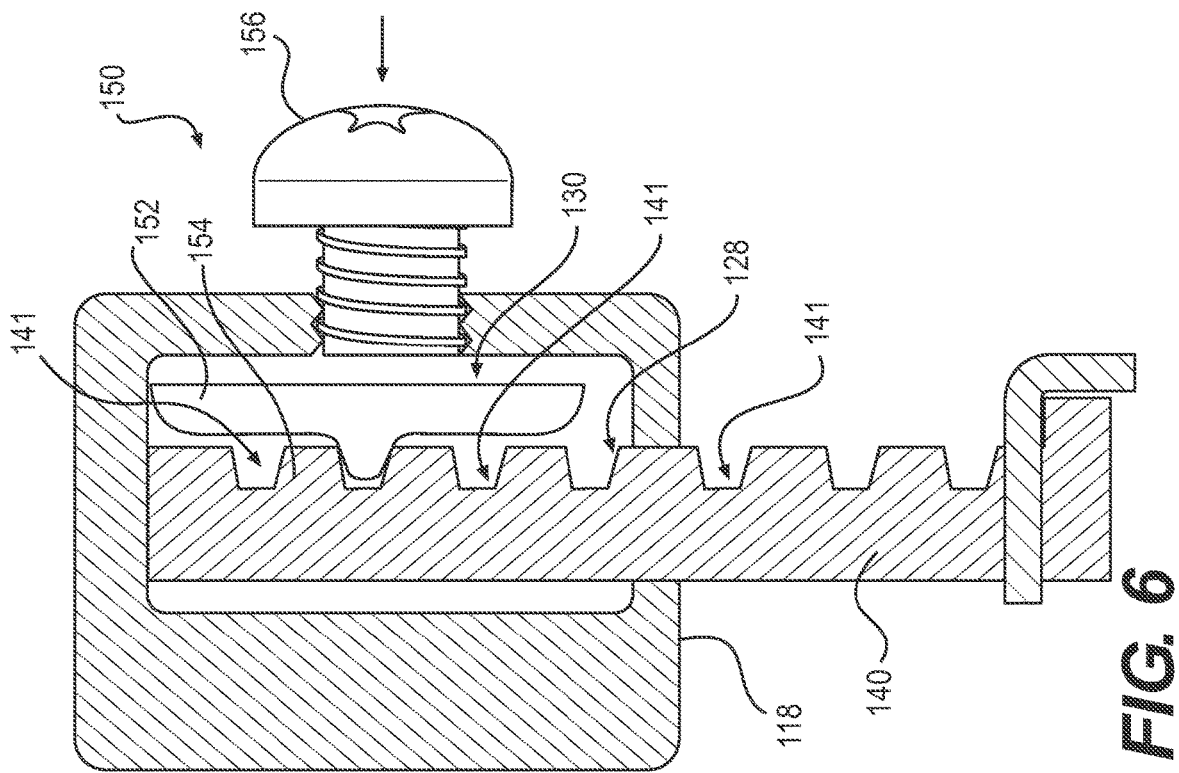
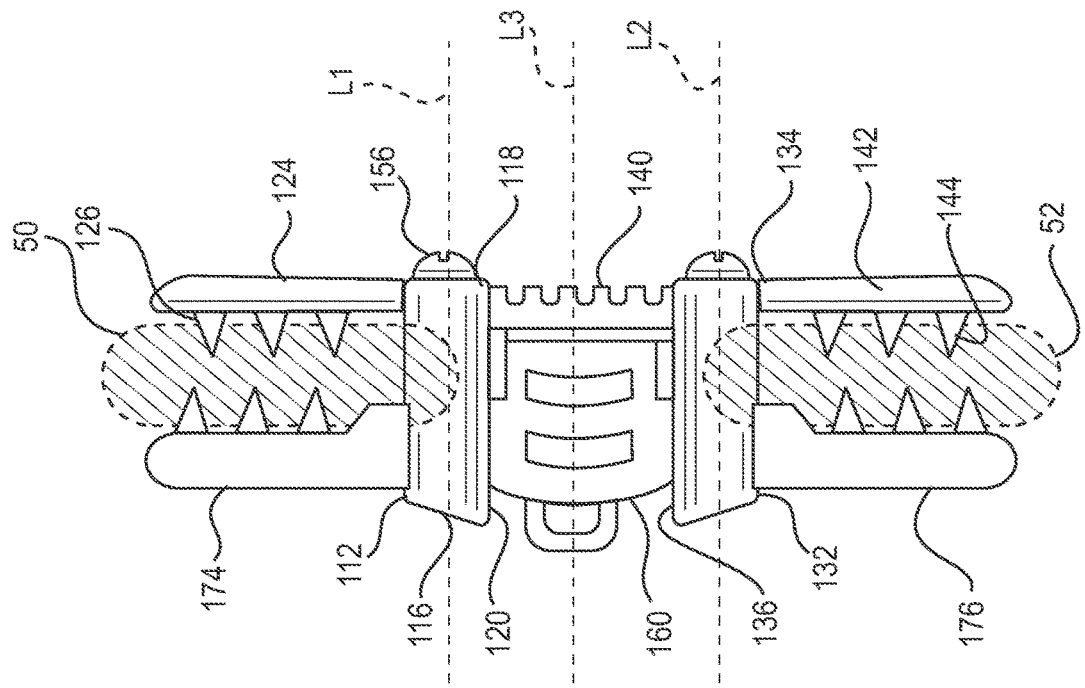

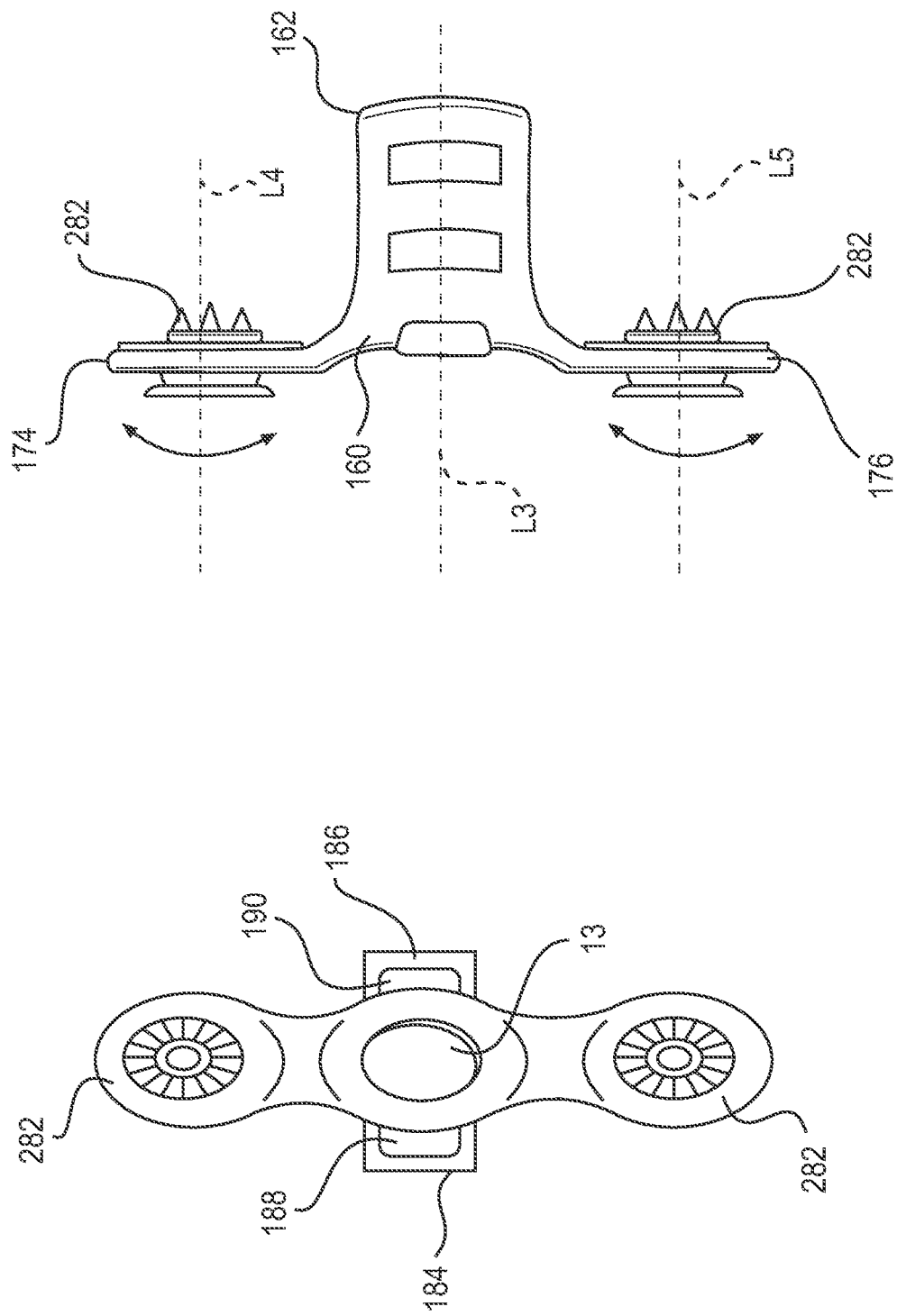

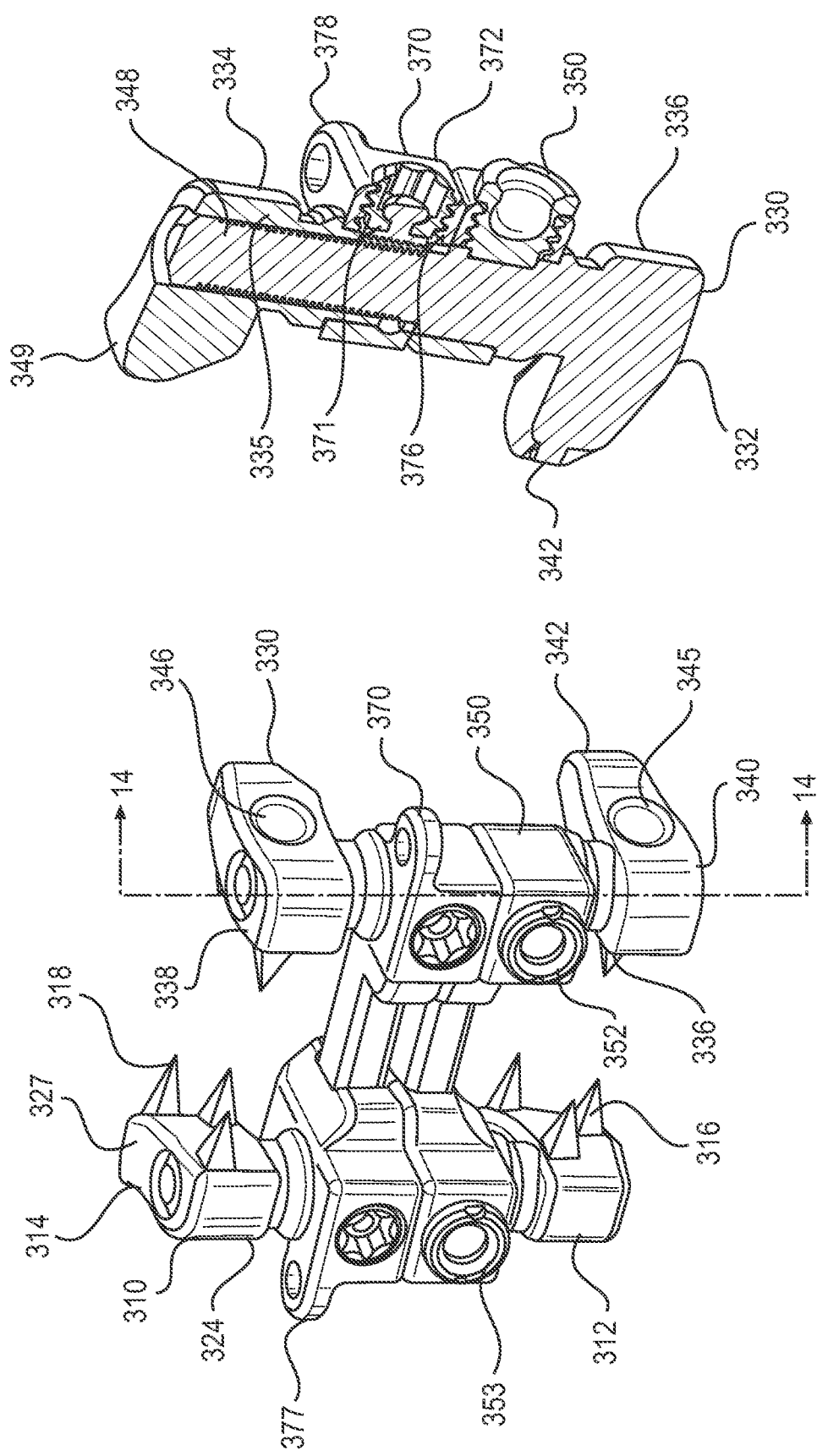

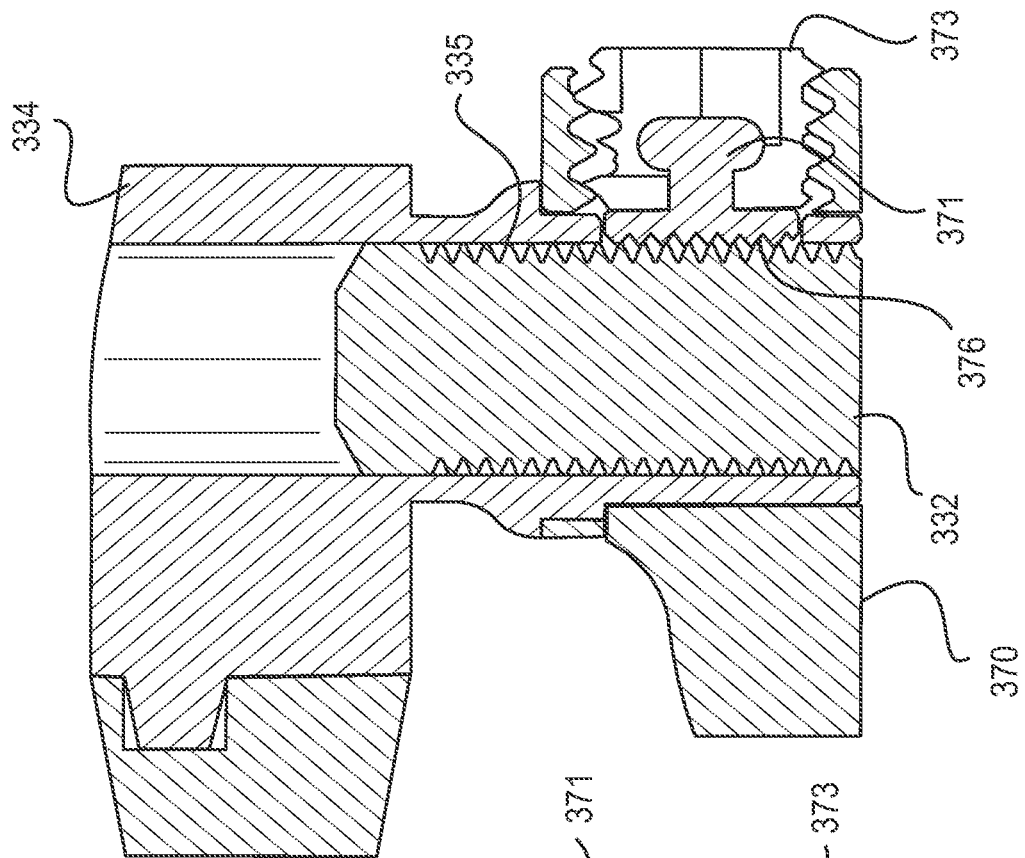
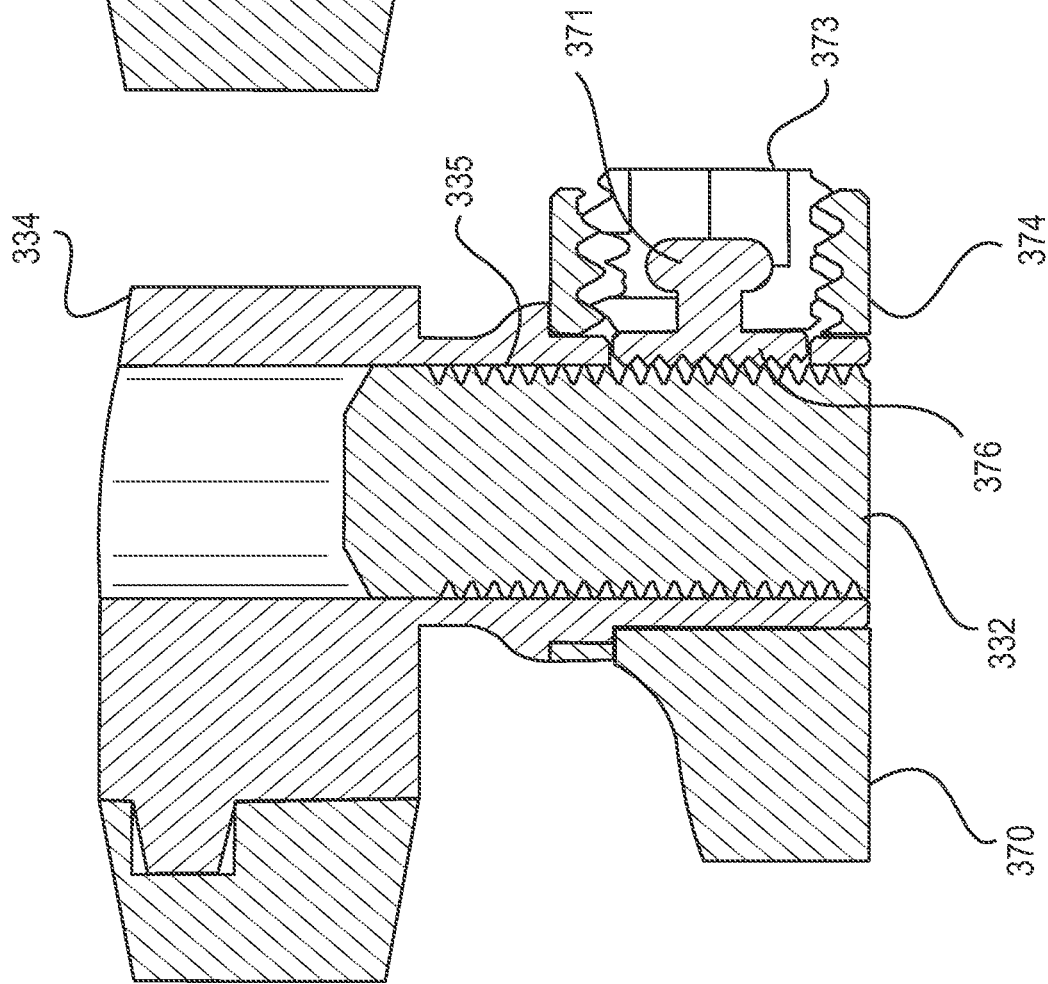

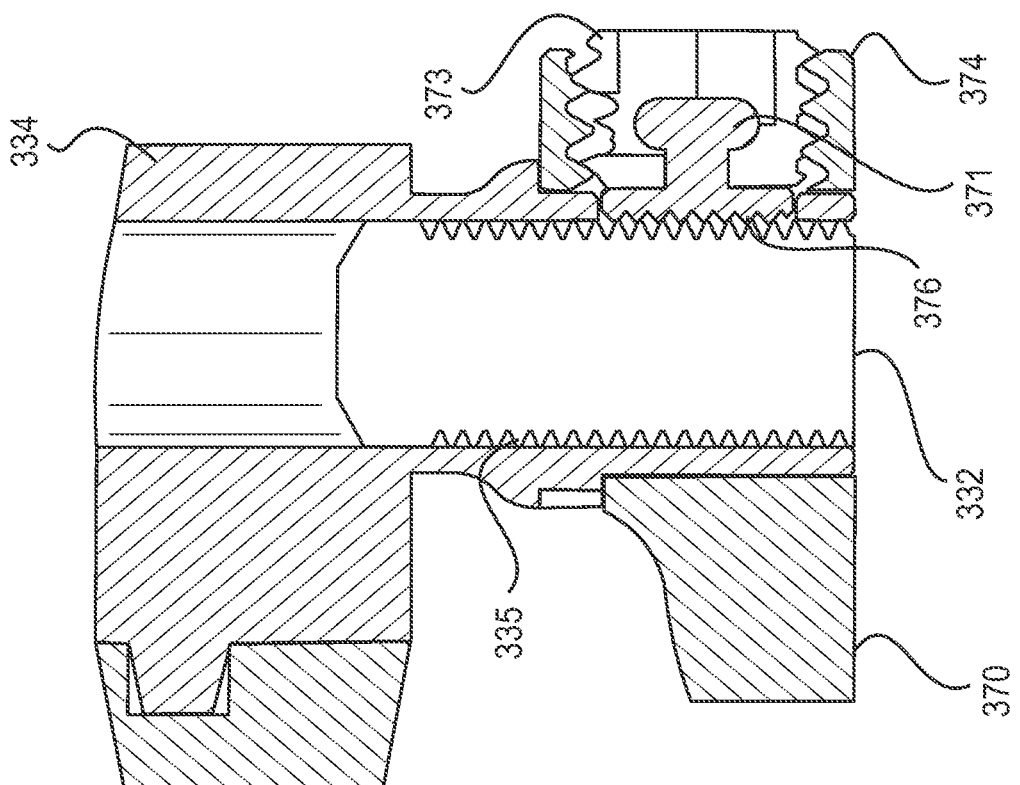
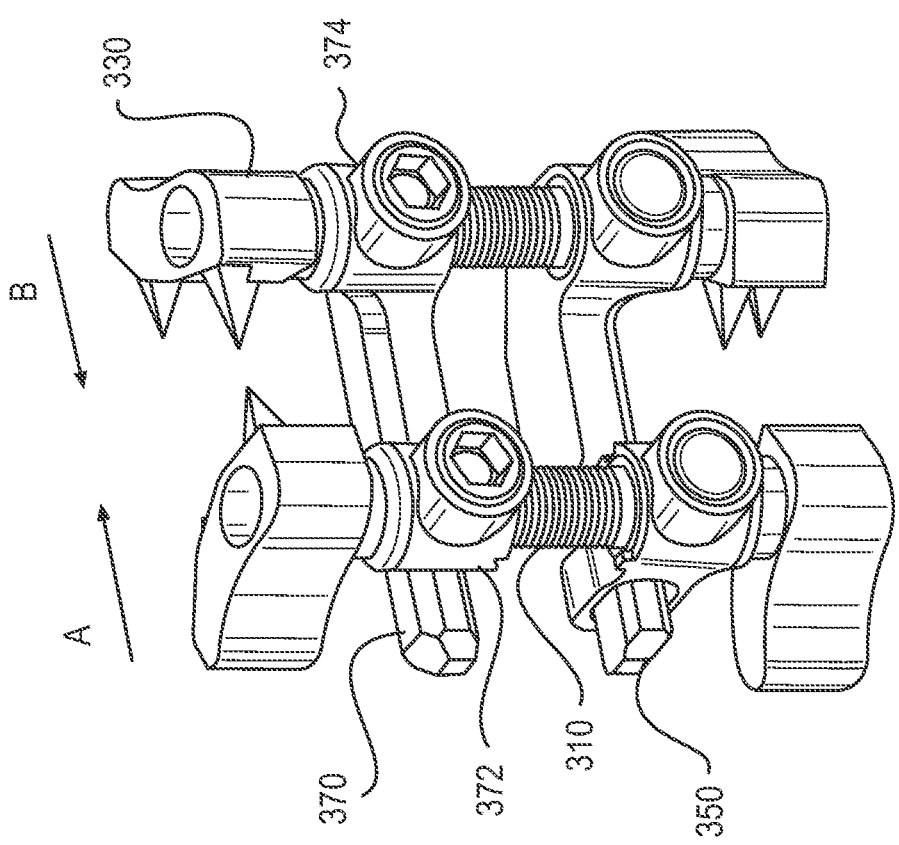
FIG. 16D
FIG. 16C

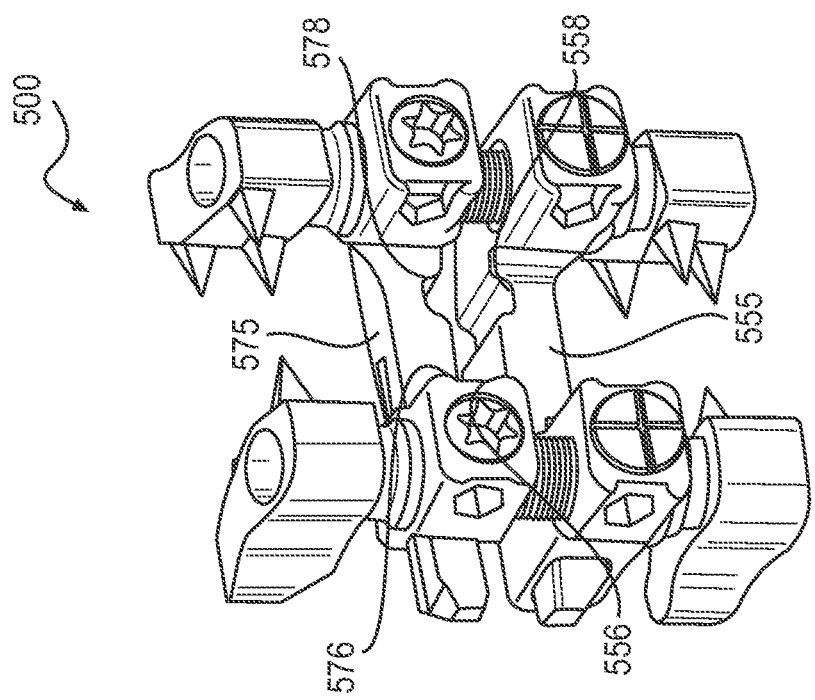
FIG. 18
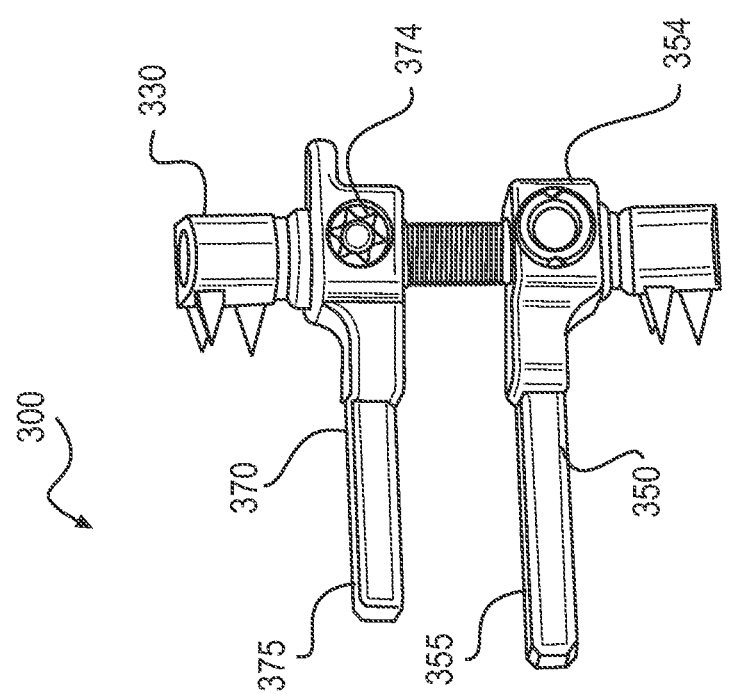
FIG. 17
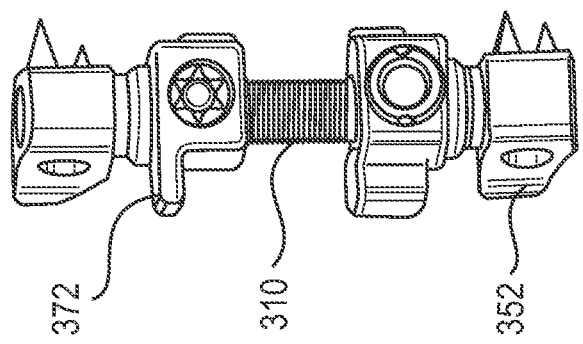

EXPANDABLE SPINAL FIXATION SYSTEM

CROSS-REFERENCE TO RELATED APPLICATION

The present application is a Continuation of U.S. patent application Ser. No. 16/728,246, filed on Dec. 27, 2019 (published as U.S. Pat. Pub. No. 2020-0146730), which is a Continuation of U.S. patent application Ser. No. 15/960,614, filed Apr. 24, 2018, now U.S. Pat. No. 10,548,647, which is a Continuation of U.S. patent application Ser. No. 15/072,664, filed Mar. 17, 2016, now U.S. Pat. No. 9,974,575, which is a Continuation-in-Part of U.S. patent application Ser. No. 15/012,992, filed on Feb. 2, 2016, now U.S. Pat. No. 9,622,793, the contents of all of which are incorporated herein in their entireties by reference for all purposes.

BACKGROUND

Field of the Invention

The present invention relates to spinous process fixation systems.

Description of the Related Art

A variety of medical devices and medical device systems may be implanted within a body of a patient to provide support to a portion or portions of the patient's body. For example, some medical devices may be implanted and coupled to backbones or portions of the spine of a patient, and may be configured to provide support to the spinal bone structure of the patient.

Typically, weaknesses in the spine are corrected using devices that fuse one or more vertebrae together. It may be desirable to have an implantable device that provides for structural stability two adjacent vertebrae and to achieve supplemental fusion to treat weaknesses in the spine due to degenerative disc disease, spondylolisthesis, trauma (i.e., fracture or dislocation), tumors and/or other causes.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, an expandable spinal fixation system may include an expandable barrel assembly having an upper barrel half and a lower barrel half. The upper barrel half includes an upper barrel distal end and an upper barrel proximal end, distal from the distal end. The upper barrel proximal end includes a slot formed therein and a concave inner surface extending between the upper barrel distal end and the upper barrel proximal end. The lower barrel half includes a lower barrel distal end and a lower barrel proximal end, distal from the lower barrel distal end. The lower barrel proximal end includes a tab sized to be slidably inserted into the slot and a concave inner surface extending between the lower barrel distal end and the lower barrel proximal end. A securing assembly includes a plate adapted to bias the tab against the upper barrel proximal end and a securing member adapted to releasably bias the plate against the tab. A fixed barrel assembly has a generally tubular body sized to fit between the concave inner surface of the upper barrel half and the concave inner surface of the lower barrel half.

In one embodiment, the expandable spinal fixation system includes an expandable barrel assembly having an upper barrel half extending along an upper longitudinal axis and a lower barrel half extending along a lower longitudinal axis generally parallel to the upper longitudinal axis. The lower longitudinal axis is movable relative to the upper longitudinal axis. A fixed barrel assembly is adapted to be inserted between the upper barrel half and a lower barrel half.

In an alternative embodiment, the expandable spinal fixation system includes a fixed barrel assembly and an expandable barrel assembly having an upper barrel half and a lower barrel half slidingly coupled to the upper barrel half, such that the fixed barrel assembly is insertable between the upper barrel half and the lower barrel half and that the lower barrel half slidable toward the upper barrel half to secure the fixed barrel assembly between the upper barrel half and the lower barrel half.

In yet another alternative embodiment, an expandable fixation system comprises a first longitudinal member and a second longitudinal member extending generally parallel to the first longitudinal member and being adjustable relative to the first longitudinal member. A first lateral member has a first end slidingly disposed along the first longitudinal member and a second end fixedly disposed along the second longitudinal member. A second lateral member has a first end slidingly disposed along the first longitudinal member and a second end fixedly disposed on the second longitudinal member, such that the second lateral member extends generally parallel to the first lateral member.

In still another alternative embodiment, an expandable spinal fixation system comprises an expandable barrel assembly having an upper barrel half having. The upper barrel half includes an upper barrel proximal end and an upper barrel distal end, distal from the proximal end. A lower barrel half includes a lower barrel proximal end and a lower barrel distal end, distal from the lower barrel proximal end. A fixed barrel assembly has a body sized to fit between the upper barrel half and the lower barrel half in one of an anterior-to-posterior direction and a lateral direction.

In yet another alternative embodiment, an expandable spinal fixation system comprises expandable barrel assembly and the fixed barrel assembly described above, as well as an insertion tool adapted to releasably engage the upper barrel half and a second finger adapted to releasably engage the lower barrel half such that operation of the insertion tool vertically adjusts the upper barrel half with respect to the lower barrel half.

In still another alternative embodiment, a method of inserting the inventive fixation system is provided.

BRIEF DESCRIPTION OF THE DRAWINGS

Other aspects, features, and advantages will become more fully apparent from the following detailed description, the appended claims, and the accompanying drawings in which like reference numerals identify similar or identical elements.

FIG. 5 is a side elevational view of the spinal fixation system shown in FIG. 1, having been inserted between the two adjacent spinal processes;

FIG. 6 is an enlarged side elevational view of an adjustable locking mechanism of the expandable barrel assembly shown in FIG. 3;

FIG. 7 is a rear elevational view of an alternative embodiment of a fixed barrel assembly for use with the spinal fixation system shown in FIG. 1;

FIG. 8 is a side elevational view of the fixed barrel assembly shown in FIG. 7;

FIG. 13 is an upper perspective view of the expandable fixation system shown in FIG. 12, in a vertically contracted condition;

FIG. 14 is a sectional view of the expandable fixation system taken along lines 14-14 of FIG. 13;

FIG. 16A is an enlarged sectional view of the securing member of the expandable fixation system shown in FIG. 14 in an unsecured condition;

FIG. 16B is an enlarged sectional view of the securing member of the expandable fixation system shown in FIG. 14 in a lightly secured condition;

FIG. 16C is a perspective view of the expandable fixation system shown in FIG. 12, in a vertically expanded condition;

FIG. 16D is an enlarged sectional view of the securing member of the expandable fixation system shown in FIG. 14 in a tightly secured condition;

FIG. 17 is a front perspective view of the expandable fixation system shown in FIG. 12 in a separated condition;

FIG. 18 is a front perspective view of another alternative embodiment of the fixation system shown in FIG. 12;

DETAILED DESCRIPTION

Figure 1:
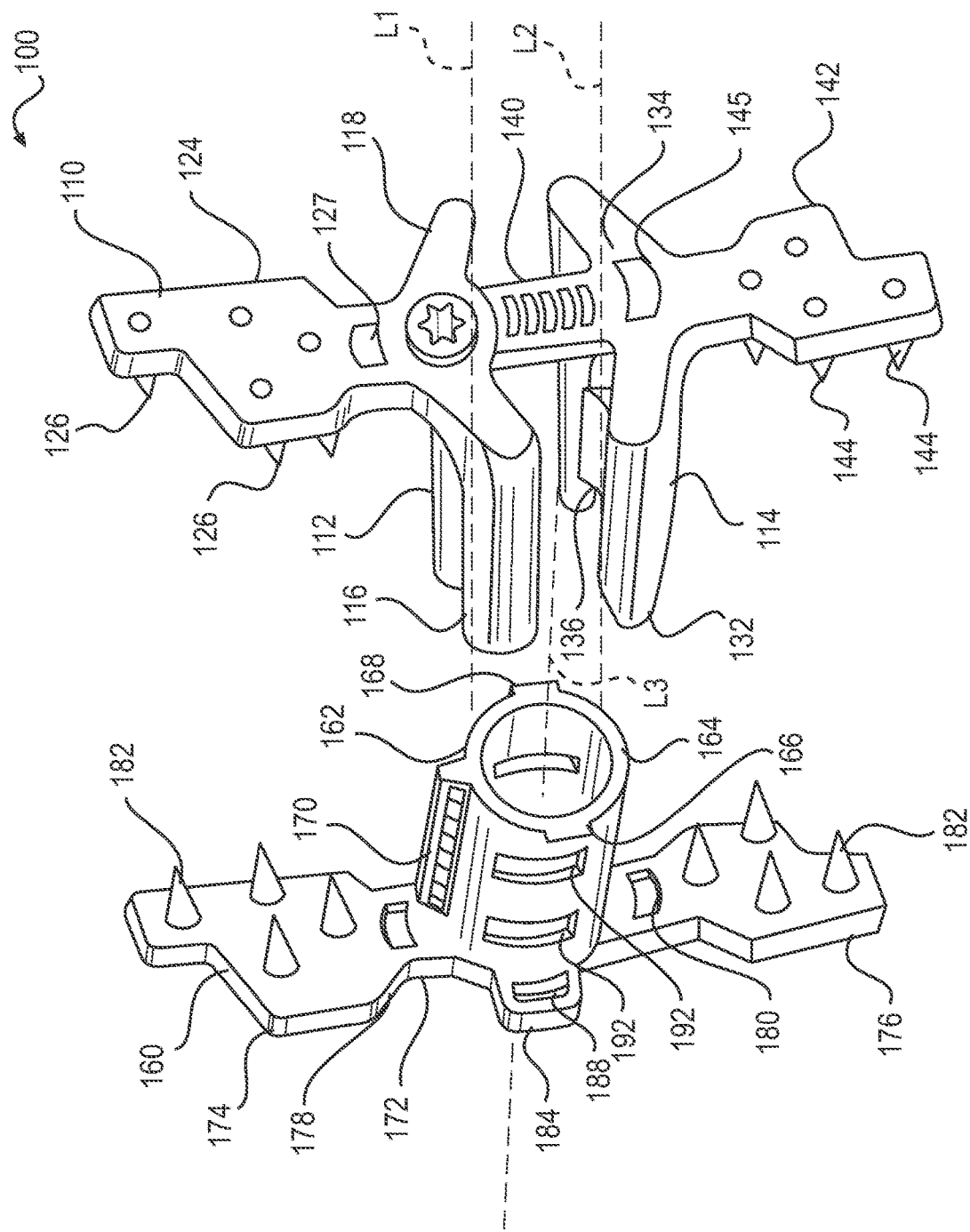
FIG. 1 is a perspective view of a first exemplary embodiment of an expandable spinal fixation system.

In the drawings, like numerals indicate like elements throughout. Certain terminology is used herein for convenience only and is not to be taken as a limitation. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment. The appearances of the phrase "in one embodiment" in various places in the specification are not necessarily all referring to the same embodiment, nor are separate or alternative embodiments necessarily mutually exclusive of other embodiments.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The devices and methods described herein are generally directed to medical devices that can be used to support, stabilize and/or replace anatomical structures within a body of a patient. In some implementations, the devices and methods described herein are configured to provide support to a spine or back of a patient, including providing support between two vertebrae in the spine or back of the patient. In other implementations, other portions of the body of the patient can be supported by the devices described herein. The medical devices described herein may be implanted within a body of a patient to assist in maintaining normal physiologic motion in the spine of the patient.

The term patient may be used hereafter for a person who benefits from the medical device or the methods disclosed herein. For example, the patient may be a person whose body receives the medical device disclosed herein in a surgical treatment. For example, in some embodiments, the patient may be a human female, human male, or any other mammal.

This document describes implementations of an implantable medical device that may be used as a posterior, non-pedicle supplemental fixation device for use in the non-cervical spine. The medical device may be used as an interspinous fusion device. The medical device may be implanted with or without the removal of the supraspinous ligament. In one or more implementations, as will be discussed below, the supraspinous ligament may be preserved. The medical device may be attached firmly to the spinous processes above and below an interspinous space. The medical device may immobilize a lumbar motion segment posteriorly with no other devices implanted. The medical device may withstand compressive, torsional and shear loads seen in the lumbar spine. The medical device may be used to achieve supplemental fusion and to treat conditions of the spine such as, for example, degenerative disc disease, spondylolisthesis, trauma (i.e., fracture or dislocation), tumors and/or other conditions.

This document describes implementations of an implantable medical device, where the medical device may include a fixed central barrel and an expandable outer barrel with separate upper and lower barrel halves, with each barrel and barrel half having bone contacting endplates. The plates include projections (e.g., spikes) that bite into the spinous process to clamp the device in place. The barrels may angulate relative to each other to conform to the patient anatomy. The plates may be locked with a set screw and may have a lordotic profile to match the lumbar anatomy. The expandable outer barrel may provide interspinous distraction, off-loading the spikes on the plate and reducing the chances of breaking the spinous process. The outer barrel may be sized to fit into the interspinous space without resistance, and then expanded. The central barrel may include a graft window anteriorly and posteriorly and may be packed with graft material after expansion using the graft window. The endplates may include anatomically-shaped grooves for optimal bone contact and fit. Optionally, the endplates may be omitted.

In an exemplary embodiment, the device may be constructed from titanium. Optionally, the expandable outer barrel and the fixed central barrel can be constructed from other material, such as, for example, polyether ether ketone (PEEK) or other suitable biocompatible material.

The present disclosure provides embodiments of expandable spinal fixation assemblies that can be used to achieve supplemental spinal fusion and treating, among others, the following conditions: degenerative disc disease; spondylolisthesis; trauma (i.e., fracture or dislocation); and/or tumor.

Referring to FIGS. 1-11, an expandable spinal fixation system 100 ("fixation system 100") for immobilizing two adjacent spinous processes 50, 52, such as, for example, vertebrae in the non-cervical spine, according to a first exemplary embodiment is shown. As used throughout this text, spinous process 50 is an upper vertebra and spinous process 52 is a lower vertebra, although those skilled in the art will recognize that spinous processes 50, 52 can be other biological elements instead.

Figure 3:
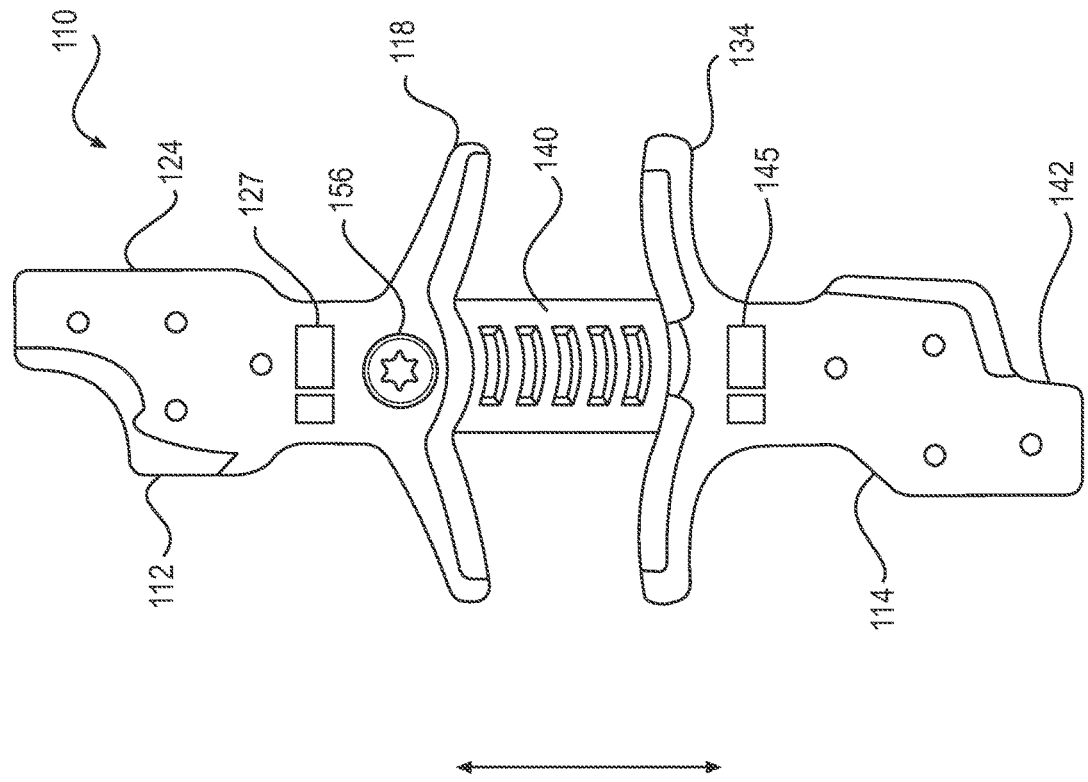
FIG. 3 is a front elevational view of the expandable barrel assembly shown in FIG. 2, in an expanded condition.
Figure 2:
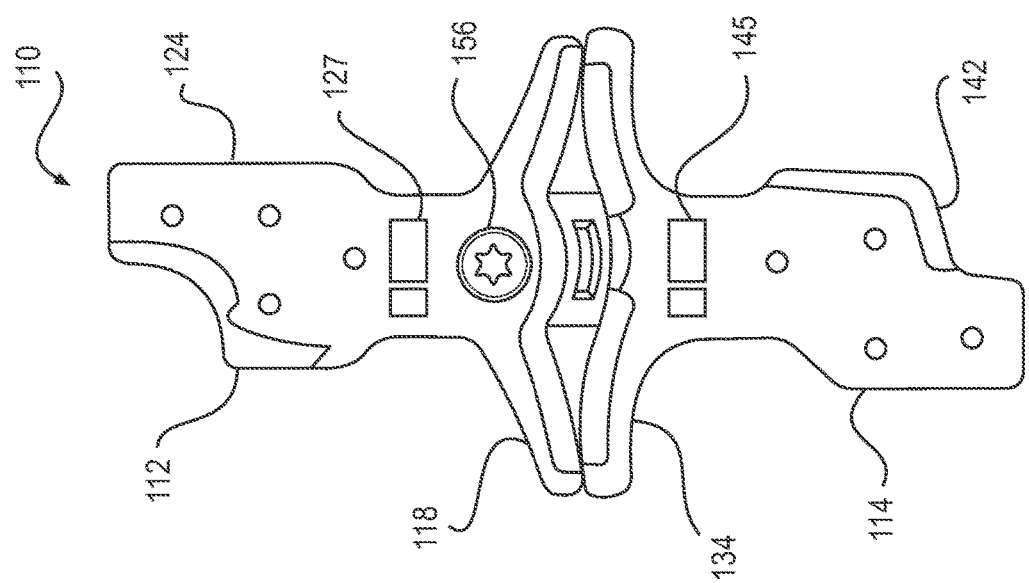
FIG. 2 is a front elevational view of an expandable barrel assembly of the system shown in FIG. 1, in a pre-expanded condition.

Fixation system 100 includes an expandable barrel assembly 110 having an upper barrel half 112 that is releasably securable to a lower barrel half 114 such that upper barrel half 112 and lower barrel half 114 can vertically translate with respect to each other, as shown in FIGS. 2 and 3.

Figure 4:
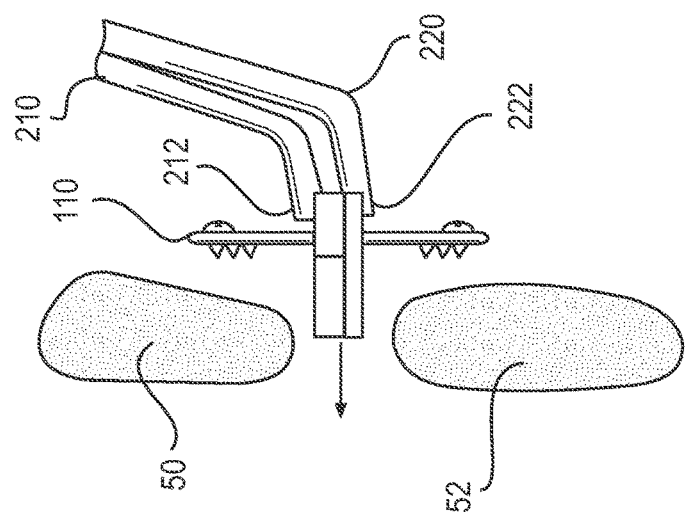
FIG. 4 is a side elevational view of the expandable barrel assembly shown in FIG. 2, being inserted between two adjacent spinal processes.

Expandable barrel assembly 110 is adapted to be inserted between two adjacent spinal processes 50, 52, as shown in FIG. 4. Fixation system 100 also includes a fixed barrel assembly 160 such that fixed barrel assembly 160 is adapted to be inserted between upper barrel half 112 and lower barrel half 114.

Referring back to FIG. 1, as well as to FIG. 5, barrel half 112 extends along an upper longitudinal axis L1 and has an upper barrel distal end 116 and an upper barrel proximal end 118, distal from distal end 116. Upper barrel half 112 includes a generally concave inner surface 120 extending between the upper barrel distal end 116 and the upper barrel proximal end 118. A slot 122 is formed along the longitudinal length of concave inner surface 120.

Upper barrel proximal end 118 comprises an upper plate 124 extending in a first direction generally orthogonally from upper barrel half 112. Upper plate 124 is used to secure spinous process 50 to fixation system 100. Upper plate 124 may include multiple projections 126 (e.g., spikes). While the term spikes may be used for projections 126, other types of projections may be used that may have a more tapered point or rounded point or other type of ending to each projection 126. Projections 126 may be integrally formed with upper plate 124 or projections 126 may be separate components that are secured to upper plate 124. Projections 126 may be pyramid shaped with a base portion secured or integrally formed on upper plate 124. The sides of projections 126 may extend from the base to form a point in the shape of a pyramid. In other example implementations, projections 126 may be formed into other shapes that raise to a point to enable each projection 126 to engage spinous process 50. As discussed above, the end of each projection 126 may include tips other than a point such as, for example, rounded tip, a square tip or other-shaped tip.

While projections 126 are shown in FIG. 1 as being fixed, those skilled in the art will recognize that projections 126 may also be articulating projections that provide various degrees of angular articulation as may be required by the particular anatomy of the patient into which fixation system 100 is being inserted.

In an exemplary embodiment, upper plate 124 and projections 126 may be made of titanium. In other implementations, upper plate 124 and projections 126 may be made of other biocompatible materials. Upper plate 124 includes a recess 127 formed therein, which sized to accept a distractor insert, as will be discussed later herein.

Referring to FIG. 6, a vertical slot 128 is formed upper barrel proximal end 118, and extends upwardly into plate 124. A threaded hole 130 is formed upper plate 124 and provides communication with vertical slot 128.

Referring back to FIGS. 1 and 5, lower barrel half 114 extends along a lower longitudinal axis L2 generally parallel to upper longitudinal axis L1, wherein lower longitudinal axis L2 is movable relative to upper longitudinal axis L1. Lower barrel half 114 also includes a lower barrel distal end 132 and a lower barrel proximal end 134, distal from lower barrel distal end 132. Lower barrel half 114 includes a generally concave inner surface 136 extending between lower barrel distal end 132 and lower barrel proximal end 134.

Lower barrel proximal end 134 includes a tab 140 sized to be slidably inserted into slot 128 such that lower barrel half 114 is slidingly coupled to upper barrel half 112 such that lower barrel half 114 is slidable toward upper barrel half 112 to secure fixed barrel assembly 160 between upper barrel half 112 and lower barrel half 114. Tab 140 includes a plurality of laterally extending recesses 141 extending along a proximal side thereof.

Lower barrel proximal end 134 also includes a lower plate 142 extending in a second direction, opposite the first direction of the extension of upper plate 124, generally orthogonally from lower barrel half 114. Similar to projections 126 extending distally outwardly from upper plate 124, lower plate 142 includes a plurality of projections 144 extending distally outwardly therefrom. Lower plate 142 also includes a recess 145 formed therein, which is sized to accept a distractor insert, as will be discussed later herein.

While expandable barrel assembly 110 includes upper plate 124 and lower plate 142, those skilled in the art will recognize that upper plate 124 and lower plate 142 can be omitted, allowing the natural compression between spinous processes 50, 52, as well as fixed barrel 160, to retain expandable barrel assembly 110 in place after its insertion.

Referring now to FIG. 6, barrel assembly 110 further includes a securing assembly 150 having a plate 152 that is adapted to releasably bias tab 140 against upper barrel proximal end 118 to secure upper barrel half 112 to lower barrel half 114 and to assist in securing spinous processes 50, 52 to fixation system 100. Plate 152 includes a laterally extending rib 154 that is sized to fit into one of recesses 141.

A securing member 156 is adapted to releasably bias plate 152 against tab 140. Securing member 156 can be a screw that is threadably inserted through a threaded hole 130 to allow for releasable biasing of plate 152 against tab 140. When securing member 156 biases plate 152 against tab 140, lower barrel half 114 is fixed relative to upper barrel half 112.

Referring now to FIGS. 1, 5, 7, and 8, fixed barrel assembly 160 is adapted to be inserted between upper barrel half 112 and lower barrel half 114. Fixed barrel assembly 160 has a generally tubular body 162 sized to fit between convex inner surface 120 of upper barrel half 112 and concave inner surface 136 of the lower barrel half 114. Body 162 extends along a longitudinal axis L3.

Fixation system 100 can include a plurality of fixed barrel assemblies 160 having bodies 162 of different external diameters to accommodate different amounts of distraction required between adjacent spinal processes 50, 52.

Body 162 comprises a distal end 164 having a first tang 166 extending outwardly laterally therefrom and a second tang 168 extending outwardly laterally therefrom, diametrically opposed from first tang 166. Tangs 166, 168 act as spacers between upper barrel half 112 and lower barrel half 114 and as a fulcrum, as will be described in more detail later herein.

Figure 3A:
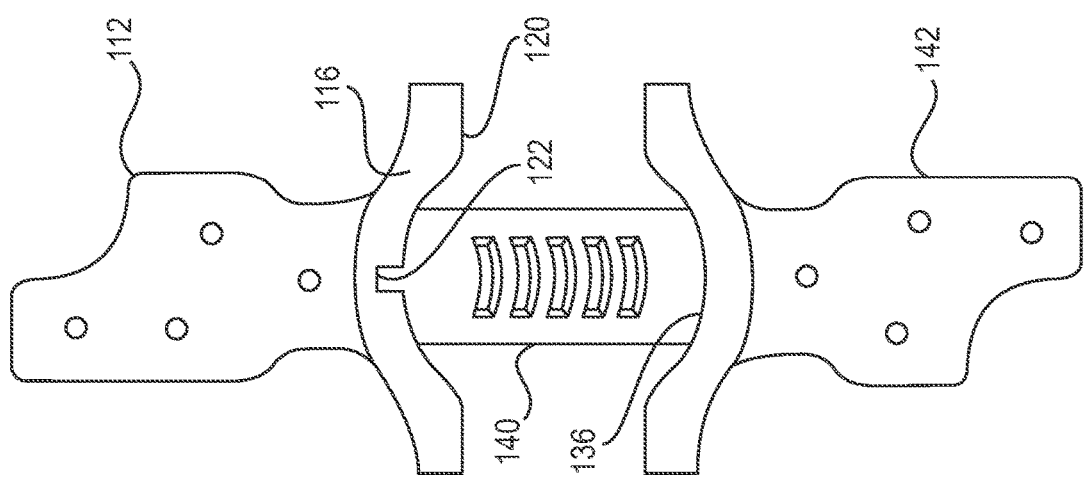
FIG. 3A is a rear elevational view of the expandable barrel assembly shown in FIG. 2, in an expanded condition.

Body 162 also includes a key 170 extending longitudinally along at least a portion thereof. Referring to FIG. 3A, slot 122 in concave inner surface 120 of upper barrel half 112 is adapted to receive key 170 when fixed barrel assembly 160 is inserted into expandable barrel assembly 110.

Body 162 further includes a proximal end 172 having a first securing plate 174 extending away from body 162, generally orthogonal to longitudinal axis L3, and a second securing plate 176 extending away from body 162, generally co-planar with first securing plate 174. Each of first and second securing plates 174, 176 includes a locking recess 178, 180, respectively extending therethrough, such that each locking recess 178, 180 is sized to allow for insertion upper barrel distal end 116 and lower barrel distal end 132, respectively. Similar to projections 126 and 144 discussed above, each of the first and second securing plates 174, 176 also includes articulating spikes or projections 182 extending outwardly distally therefrom. Projections 182 are used to engage fixed barrel assembly 160, with spinous processes 50, 52.

Instead of fixed projections 182, in an alternative embodiment, articulating spikes 282 may be used, as shown in FIGS. 6 and 7. As shown in FIG. 8, articulating spikes 282 can pivot about longitudinal axes L4, L5 to accommodate a firm connection to spinal processes 50, 52, respectively.

Proximal end 172 also includes a first proximal wing 184 and a second proximal wing 186 extending outwardly therefrom, such that each of first proximal wing 184 and second proximal wing 186 has a recess 188, 190, respectively formed therein. Recesses 188, 190 are adapted to receive an insertion tool, as will be discussed later herein.

Body 162 includes a plurality of radially extending windows 192 extending between distal end 164 and proximal end 172. The interior of body 162 and windows 192 may be used as graft windows for the packing of bone graft material prior to or subsequent to the insertion and placement of fixation system 100 in the patient.

According to one embodiment, a method of installing fixation system 100, for example, at the site of two adjacent spinous processes 50, 52 of the non-cervical spine, is provided. While those skilled in the art will recognize that the components of fixation system, i.e. expandable barrel assembly 110 and fixed barrel assembly 160, can be inserted in any order based on surgical approach, an exemplary installation process will be described below as inserting expandable barrel assembly 110 first and then inserting fixed barrel assembly 160 afterward. In principle, fixation system 100 is expandable in-situ, and can be locked in position between spinous processes 50, 52 by a combination of projections/spikes 126, 144, 182, 282.

Figure 9:
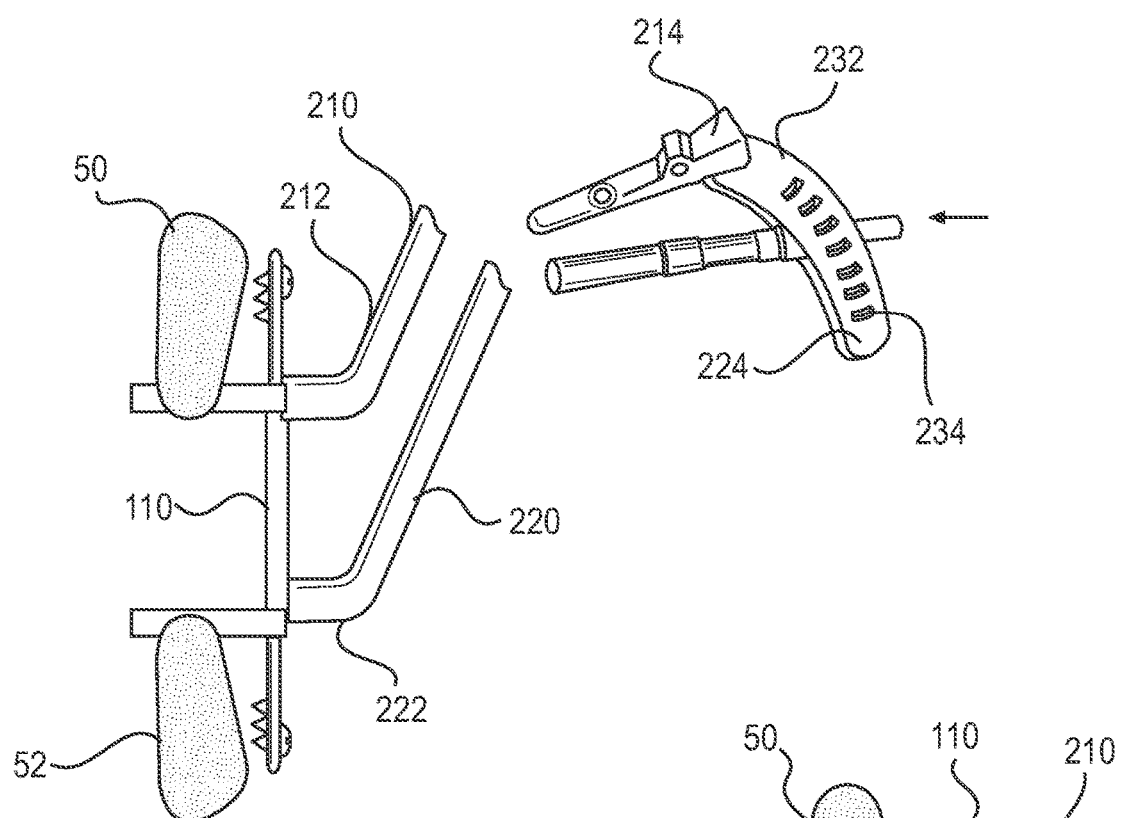
FIG. 9 is a side elevational view showing the expansion of the expandable barrel assembly shown in FIG. 2 by a distractor.
Figure 10:
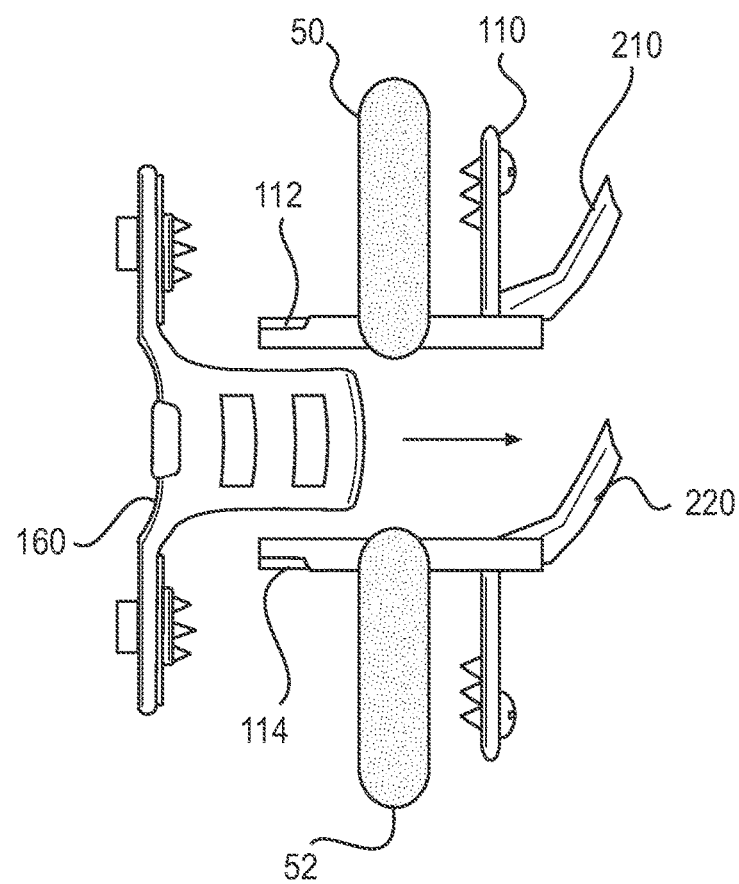
FIG. 10 is a side elevational view showing the insertion of the fixed barrel assembly shown in FIG. 1 being inserted between the expandable barrel assembly shown in FIG. 1.

As shown in FIGS. 4, 9, and 10, a distractor 200 is releasably connectable to expandable barrel assembly 110 for insertion of expandable barrel assembly 110 between adjacent spinal processes 50, 52. Distractor 200 includes a first leg 210 having a distal end 212 that is insertable into recess 127 in upper plate 124. First leg 210 also includes a proximal end 214, shown in FIG. 9. Distractor 200 further includes a second leg 220 having a distal end 222 that is insertable into recess 145 in lower plate 142. Second leg 220 also includes a proximal end 224, shown in FIG. 9.

First leg 210 is pivotally connected to second leg 220 at a pivot pin 230, such the action of moving proximal end 224 of second leg 220 toward proximal end 214 of first leg 210 spaces distal end 212 of first leg 210 away from distal end 222 of second leg 220. A barrel size gauge 232 is connected to proximal end 214, and includes indicia, such as size markings 234, that, when intersected by proximal end 224 of second leg 220, provide an indication of the distraction distance between movement of distal end 212 of first length 210 away from distal end 222 of second leg 220, and, correspondingly, a distance between spinous processes 50, 52. In an exemplary embodiment, an expansion range of greater than about 6 mm can be achieved, although those skilled in the art will recognize that other ranges can be achieved as well.

At this time, expandable barrel assembly 110 is laterally inserted between spinal processes 50, 52 in a collapsed configuration, as shown in FIG. 4, and can be pressed against spinous processes 50, 52 such that projections 126 embed into spinous process 50 and secure upper plate 124 to spinous process 50 and such that projections 144 embed into spinous process 52 and secure lower plate 142 to spinous process 52.

Additionally, securing assembly 150 can optionally be operated by screwing securing member 156 against plate 152 such that rib 154 is forced into a recess 141, thereby stabilizing expandable barrel assembly 110, and, consequently, spinous processes 50, 52 in a distracted state, enabling distractor 200 to be removed from expandable barrel assembly 110. Alternatively, securing assembly 150 does not necessarily need to be operated, and distractor 200 can remain temporarily connected to expandable barrel assembly 110, keeping upper barrel half 112 and lower barrel half 114 open in the distracted/expanded state.

While spinous processes 50, 52 are distracted away from each other, fixed barrel assembly 160 can be laterally inserted from an opposing side relative to the insertion of expandable barrel assembly 110. The size of fixed barrel assembly 160 to be used can be determined by the amount of distraction, as measured by the barrel size gauge 232 on distractor 200.

Optionally, prior to insertion of fixed barrel assembly 160, body 162 can be packed with graft material. An insertion tool (not shown) is inserted into recesses 188, 190 in their respective wings 184, 186, and, as shown in FIG. 10, fixed barrel assembly 160 is inserted between upper barrel half 112 and lower barrel half 114. Fixed barrel assembly 160 can be pivoted about key 170 and/or tangs 166, 168 during insertion to better accommodate geometry of spinous processes 50, 52 in order to attain secure placement of fixed barrel assembly 160.

Figure 11:
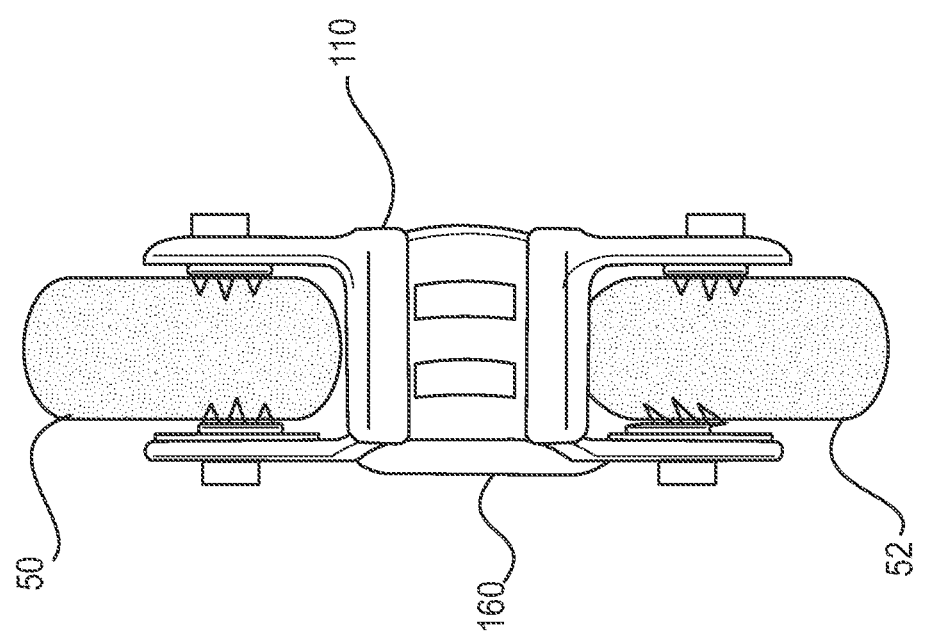
FIG. 11 is a side elevational view showing the spinal fixation system shown FIG. 1 having been inserted between adjacent spinal processes.

Once fixed barrel assembly 160 is located between upper barrel half 112 and lower barrel half 114, securing member 156 can be released, allowing natural compression of spinous processes 50, 52 to clamp down on expandable barrel assembly 110 and fixed barrel assembly 160. Fixed barrel assembly 160 can be further inserted such that distal ends 116, 132 of upper barrel half 112 and lower barrel half 114, respectively, engage recesses 178, 180, respectively in fixed barrel assembly 160 and such that projections 182 of fixed barrel assembly 160, engage spinous processes 50, 52, securing fixed barrel assembly 160 to spinous processes 50, 52, as shown in FIG. 11.

The insertion tool can then be removed from fixed barrel assembly 160 and, if distractor 200 has not yet been removed from expandable barrel assembly 110, distractor 200 can be removed at this time. If body 162 of fixed barrel assembly 160 has not yet been filled with graft material, the graft material can be inserted into body 162 at this time.

An alternative embodiment of an expandable spinal fixation system 300 ("fixation system 300") is shown in FIGS. 12-19. Fixation system 300 includes an expandable frame that is expandable in both cranial-to-caudal and left-to-right directions, with built-in spike plates to grip adjacent spinal processes. Fixation system 300 can be constructed from titanium or other biocompatible materials.

Referring specifically to FIGS. 12-15, fixation system 300 includes a first longitudinal member 310 and a second longitudinal member 330 extending generally parallel to first longitudinal member 310. Second longitudinal member 330 is adjustable relative to first longitudinal member 310 such that a spacing between first longitudinal member 310 and second longitudinal member 330 can be adjusted based on the width of spinous processes 50, 52.

A first lateral member 350 has a first collar 352 slidingly disposed along first longitudinal member 310 and a second collar 354 fixedly disposed along second longitudinal member 330. A laterally extending rod 355 is fixedly connected to second collar 354 and slidingly coupled to first collar 352 such that the distance between first longitudinal member 310 and second longitudinal member 330 can be adjusted to fit particular spinous processes 50, 52.

Similarly, a second lateral member 370 has a first collar 372 slidingly disposed along first longitudinal member 310 and a second collar 374 fixedly disposed on second longitudinal member 330. A laterally extending rod 375 is fixedly connected to second collar 374 and slidingly coupled to first collar 372 such that the distance between first longitudinal member 310 and second longitudinal member 330 can be adjusted to fit particular spinous processes 50, 52.

Second lateral member 370 extends generally parallel to first lateral member 350, such that members 310, 330, 350, 370 form an expandable and contractible rectangle, depending on the geometry of spinous processes 50, 52. Optionally, a graft window formed by the interior of the rectangle can be packed following insertion of fixation system 300 in a patient.

In different exemplary embodiments, fixation system 300 is expandable across different height ranges. By way of example, a first height range can be between about 6 millimeters ("mm") and about 12 mm; a second height range can be between about 8 mm and about 16 mm; and a third height range can be between about 10 mm and about 20 mm. Additionally, in different exemplary embodiments, fixation system 300 is expandable across different width ranges. By way of example, a first width range can be between about 6 mm and about 12 mm; and a second width range can be between about 8 mm and about 16 mm.

Figure 12:
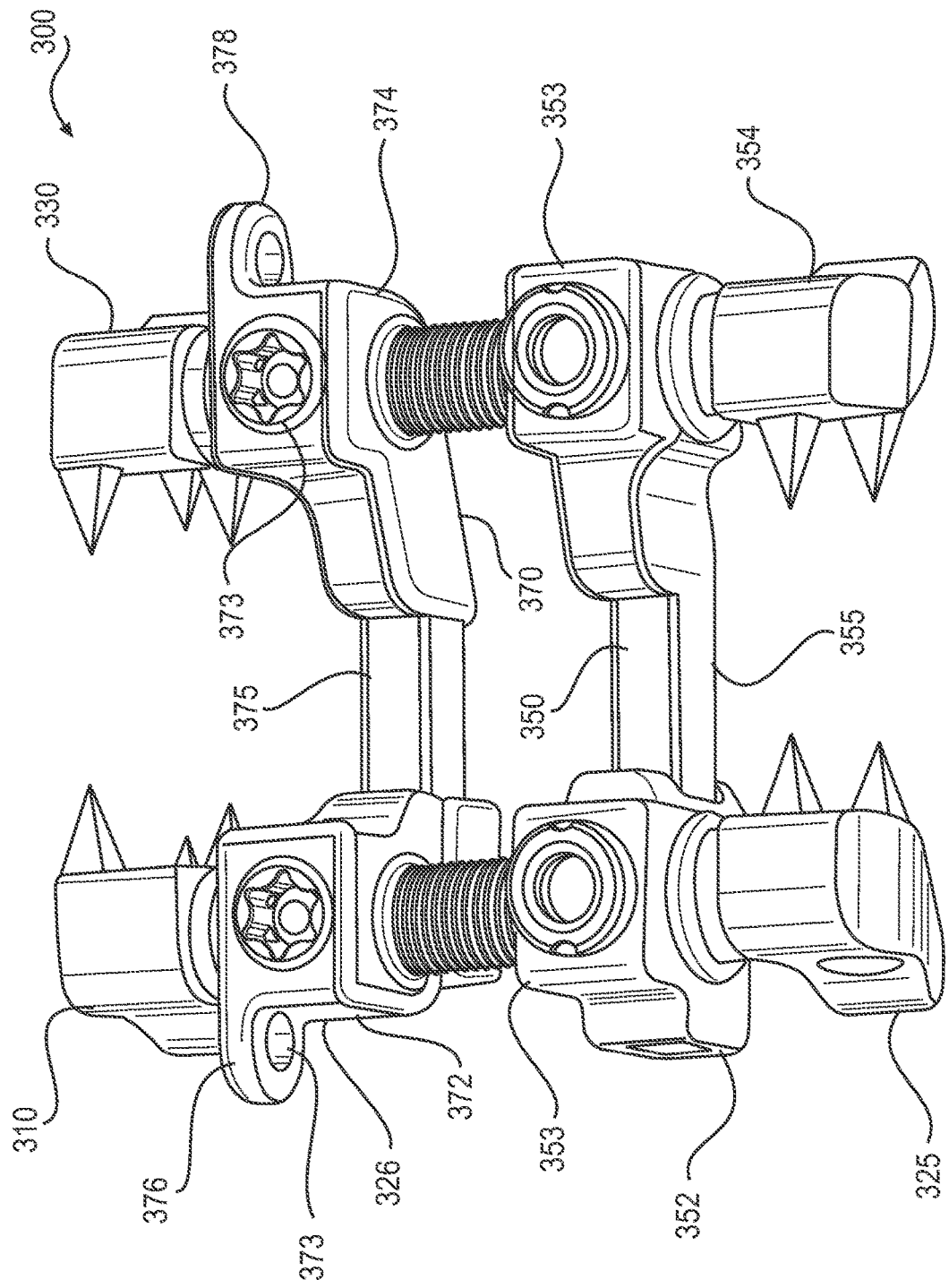
FIG. 12 is a lower perspective view of a second exemplary embodiment of expandable fixation system, in a vertically expanded condition.

In order to achieve expandability between first lateral member 350 and second lateral member 370, longitudinal members 310, 330 are expandable between an expanded condition, as shown in FIG. 12, and a contracted condition, as shown in FIG. 13. As shown in FIG. 14, second longitudinal member 330 comprises a lower portion 332 and an upper portion 334 telescopically connected to lower portion 332. Similarly, first longitudinal member 310 comprises a lower portion 312, and an upper portion 314 telescopically connected to lower portion 312.

Lower portion 312, 332, of each longitudinal member 310, 330 is releasably securable to first lateral member 350, and upper portion 314, 334 of each longitudinal member 310, 330 is releasably securable to second lateral member 370. Each of lower portion 312, 332 of first longitudinal member 310, 330 comprises a ribbed exterior (only ribbed exterior 335 in second longitudinal member 330 is shown).

Referring back to FIGS. 12 and 13, as well as FIG. 14, lower portion 312 includes a first spiked member 316 extending medially therefrom. Upper portion 314 includes a second spiked member 318 extending medially therefrom. First spiked member 316 comprises a posterior connected end 320 that is connected to lower portion 312 and an anterior free end 322. Second spiked member 318 comprises a posterior connected end 328 that is connected to upper portion 314 and an anterior free end 329. Each of first spiked member 316 and second spiked member 318 comprises a lateral cavity 325, 326, respectively, disposed between posterior connected end 320 and anterior free end 322 of first spiked member 316 and between posterior connected end 328 and anterior free end 329 of second spiked member 318.

While FIG. 13 shows three spikes on each of spiked members 316, 318, those skilled in the art will recognize that spiked members 316, 318, can have more or less than three spikes each. Similar to first spiked member 316, second spiked member 318 also comprises a posterior fixed end 324 and an anterior free end 327. The spikes on spiked members 316, 318 are used to fixedly secure first longitudinal member 310 to spinous processes 50, 52. As fixation device 300 is being located on the patient's spine, spiked members 316, 318 are driven into spinous processes 52, 50, respectively, to secure fixation device 300 to the spine.

Similar to first longitudinal member 310, second longitudinal member 330 includes a first spiked member 336 extending medially therefrom. Upper portion 334 includes a second spiked member 338 extending medially therefrom. First spiked member 336 comprises a posterior connected end 340 that is connected to lower portion 322 and an anterior free end 342. Second spiked member 338 comprises a posterior connected end 348 that is connected to upper portion 334 and an anterior free end 349. Each of first spiked member 336 and second spiked member 338 comprises a lateral cavity 345, 346, respectively, disposed between posterior connected end 340 and anterior free end 342 of first spiked member 336 and between posterior connected end 348 and anterior free end 349 of second spiked member 338.

In an exemplary embodiment, a first configuration of a securing member 353 is adapted to releasably secure first lateral member 350 to lower portion 312 of first longitudinal member 310 and to lower portion 332 of second longitudinal member 330. As shown in FIG. 12, securing member 353 can be a screw that requires a spanner wrench (not shown) to rotate. Further, a second configuration of a securing member 373 can be adapted to releasably secure second lateral member 370 to upper portion 314 of first longitudinal member 310 and to upper portion 334 of second longitudinal member 330. As shown in FIG. 12, securing member 373 can be a screw that requires a TORX® wrench (not shown) to rotate. Alternatively, as shown in FIGS. 16A-16D, securing member 373 can be an Allen head screw. Additionally, as shown in FIG. 14, second lateral member 370 securing member 373 includes an insert 371 that has a ribbed engagement surface 376 adapted to releasably engage ribbed exterior 335 of lower portion 332 in order to releasably secure upper portion 334 to lower portion 332. Although not shown, a similar configuration is provided with respect to first longitudinal member 310 in order to releasably secure upper portion 314 to lower portion 312.

Second lateral member 370 also includes an engagement eye 377 extending laterally from first longitudinal member 310 and an engagement eye 378 extending laterally from second longitudinal member 330.

Figure 16:
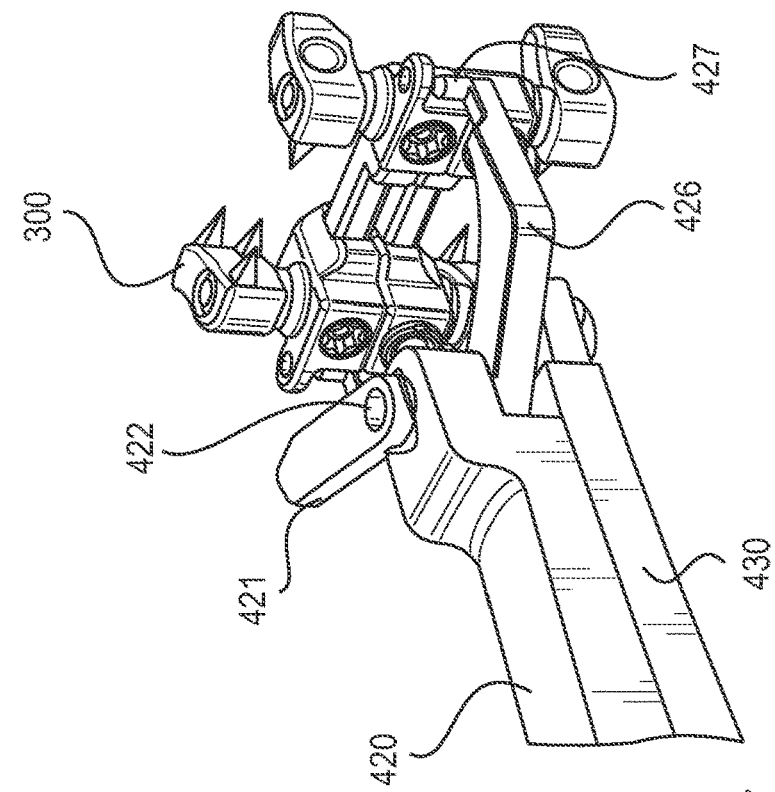
FIG. 16 is a rear perspective view of the distractor shown in FIG. 15, engaged with the expandable fixation system shown in FIG. 12.
Figure 15:
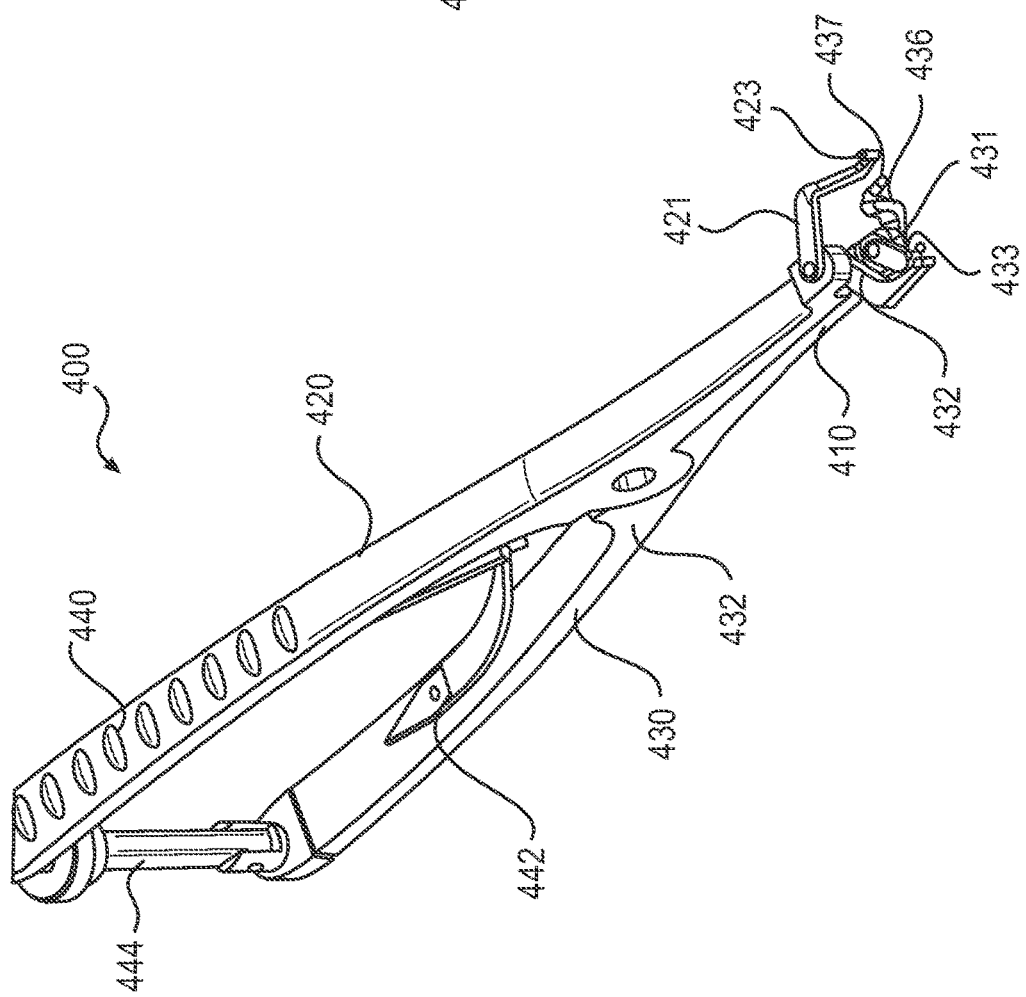
FIG. 15 is a perspective view of an exemplary embodiment of a distractor for use with the expandable fixation system shown in FIG. 12.

An exemplary distractor 400 that can be used to implant fixation device 300 into a patient (not shown) is shown in FIG. 15 and the connection of distractor 400 with fixation device 300 is shown in FIG. 16.

Distractor 400 includes a distal end 410 that is releasably connectable to fixation device 300, and a proximal end 440 that is gripped and compressed by a user to open distal end 410. Distractor 400 includes a top leg 420 that is pivotally connected to a second leg 430 at a pivot 432 such that, when proximal end 440 is compressed, distal end 410 expands so that top leg 420 and bottom leg 430 separate from each other.

Proximal end 440 includes a biasing member 442 that is disposed between top leg 420 and bottom leg 430 such that from a compressed state as described immediately above, when compression force is released, biasing member 442 biases top leg 420 and bottom leg 430 away from each other along distal end 440. In an exemplary embodiment, biasing member 442 can be a leaf spring, although those skilled in the art will recognize that biasing member 442 can be helical springs or other suitable biasing members.

Proximal end 440 also includes a scale 444 that is calibrated to determine the amount of separation between first lateral member 350 and second lateral member 370. When fixation device 300 is being inserted, the inserting surgeon can read scale 444 to determine how far spinous process 50 is being separated form spinous process 52.

Distal end 410 includes two pair of articulating insertion arms that releasably engage with fixation device 300 to attached fixation device 300 to spinous processes 50, 52. Top leg 420 includes an upper arm 421 that is pivotally connected to top leg 420 at a pivot 412. Upper arm 421 also includes a pin 423 that is sized to fit into engagement eye 377 on second lateral member 370. Top leg 420 also includes a lower arm 426 that is pivotally connected to top leg 420 along the axis of pivot 422. Lower arm 426 also includes a pin 427 that is sized to fit into engagement eye 378 on second lateral member 370.

Bottom leg 430 includes an upper arm 431 that is pivotally connected to bottom leg 430 at a pivot 432. Upper arm 431 also includes a pin 433 that is sized to fit into securing member 353 on first lateral member 350 at first longitudinal member 310. Bottom leg 430 also includes a lower arm 436 that is pivotally connected to bottom leg 430 along the axis of pivot 432. Lower arm 436 also includes a pin 437 that is sized to fit into securing member 353 on first lateral member 350 at second longitudinal member 330.

With the distance between first longitudinal member 310 and second longitudinal member 330 of fixation device 300 adjusted to accommodate the width of the specific spinal processes 50, 52 at issue, distractor 400 is attached to fixation device 300 as shown in FIG. 16. Spiked members 318, 338 are forced into spinous process 50 and spiked members 316, 336 are forced into spinous process 52. At this time, ribbed engagement surface 376 is disengaged from ribbed exterior 335, as shown in FIG. 16A. Distractor 400 is then used to separate first lateral member 350 from second lateral member 370, thus opening the distance between spinous process 50 and spinous process 52, to a position as shown in FIG. 12. With spinous process 50, 52 separated, securing members 373 on first collar 372 and second collar 374 are slightly tightened for a light interference engagement, as shown in FIG. 16B, which locks the vertical distance between first lateral member 350 and second lateral member 370, but still allows for compression of first longitudinal member 310 and second longitudinal member 330 toward each other.

Then, referring to FIG. 16C, first longitudinal member 310 is compressed in the direction of arrow "A" and second longitudinal member 330 is compressed in the direction of arrow "B" to set the lateral spacing between first longitudinal member 310 and second longitudinal member 330. Securing members 373 on first collar 372 and second collar 374 are completely tightened for a tight interference engagement, as shown in FIG. 16D, locking members 310, 330, 350, 370 in place relative to each other. Optionally, graft material (not shown) can be packed in the window defined by first longitudinal member 310, second longitudinal member 330, first lateral member 350, and second lateral member 370.

Fixation device 300 with distractor 400 is designed to be implanted using a posterior insertion method. If, however, in order to spare the ligaments, a lateral insertion is desired, fixation device 300 can be disassembled, as shown in FIG. 17, such that rails 355, 375 are separated from their respective first collars 352, 372.

First longitudinal member 310 can be inserted laterally from one side of spinous processes 50, 52, and second longitudinal member 330, with first and second lateral members 350, 370, can be inserted laterally from an opposing side of spinous processes 50, 52 such that rails 355, 375 can be inserted into their respective first collars 352, 372.

In an alternative embodiment of a fixation device 500, shown in FIG. 18, instead of connecting distractor 400 to engagement eyes 377, 378 and securing members 353, rails 555, 575 each have a pair of inwardly facing slots 556, 558, and 576, 578, respectively, into which legs of a distractor (not shown) can be inserted to separate rails 55, 575 from each other.

Referring to FIGS. 19-26, a spinous process fixation assembly 600 ("fixation assembly 600") according to a first exemplary embodiment is shown. Fixation assembly 600 is a posterior, non-pedicle supplemental fixation device, intended for use in the non-cervical spine, which allows for the alternative selection of insertion of a fixed portion from a lateral direction or from a posterior-to anterior direction. With the option to preserve the supraspinous ligament, fixation assembly 600 is intended to attach firmly to adjacent spinous processes 50, 52 and immobilize a lumbar motion segment posteriorly. Fixation assembly 600 is expected to withstand compressive, torsional, and shear loads seen in the lumbar spine.

Fixation assembly 600 includes an expandable barrel assembly 610 and a fixed barrel assembly 670 that is insertable into expandable barrel assembly 610 such that expandable barrel assembly 610 can be compressed to engage and retain fixed barrel assembly 670 therein. An insertion tool, such as a distractor 700 (shown in FIGS. 24-26) is part of fixation assembly 600 and is used to insert and to vertically adjust expandable barrel assembly 610 in situ.

Expandable barrel assembly 610 includes an upper barrel half 612 and a lower barrel half 642 such that lower barrel half 642 is vertically adjustably connected to upper barrel half 612. Upper barrel half 612 includes an upper barrel proximal end 614 and an upper barrel distal end 616, distal from proximal end 614.

Upper barrel half 612 includes a vertical plate 620 that is used to engage an upper spinous process 50 (shown in FIG. 4). Plate 620 includes a plurality of medially extending spikes (not shown for clarity) that engage spinous process 50 and secure upper barrel half 612 to spinous process 50. Plate 620 includes a posterior notch 622 for engagement with distractor 700, as will be discussed later herein.

A first generally planar arm 624 extends between the upper barrel proximal end 614 and upper barrel distal end 616. A gusset 625 extends upwardly from arm 624 and connects to plate 620, providing structural stability between arm 624 and plate 620. A first arcuate portion 628 of arm 624 extends anteriorly downwardly from arm 624.

Arm 624 at a distal end 616 of upper barrel half 612 includes a first generally U-shaped opening 626. Opening 626 is sized to allow for engagement with an upper portion of fixed barrel assembly 670.

A post 630 extends downwardly from plate 620. Post 630 includes a plurality of posteriorly facing ratchet teeth 632 and corresponding anteriorly facing ratchet teeth 634 that are used to adjust the height of upper barrel half 612 with respect to lower barrel half 642.

Lower barrel half 642 has a lower barrel proximal end 644 and a lower barrel distal end 646, distal from lower barrel proximal end 644. Lower barrel half 642 includes a vertical plate 650 that is used to engage a lower spinous process 52 (shown in FIG. 4). Plate 650 includes a plurality of medially extending spikes (not shown for clarity) that engage spinous process 52 and secure lower barrel half 642 to spinous process 52. Plate 650 includes a posterior notch 652 for engagement with distractor 700, as will be discussed later herein.

A second generally planar arm 654 extends between lower barrel proximal end 644 and lower barrel distal end 646. A gusset 655 extends downwardly from arm 654 and connects to plate 650, providing structural stability between arm 654 and plate 650. A second arcuate portion 658 of arm 654 extends anteriorly upwardly from arm 654 such that, when lower barrel half 642 and upper barrel half 612 are translated vertically toward each other, arcuate portion 658 and arcuate portion 628 form an anterior obstruction that precludes the advancement of fixed barrel assembly 670 anteriorly.

Arm 654 at distal end 646 of lower barrel half 642 includes a second generally U-shaped opening 656. Opening 656 is sized to allow for engagement with a lower portion of fixed barrel assembly 660.

Figure 22:
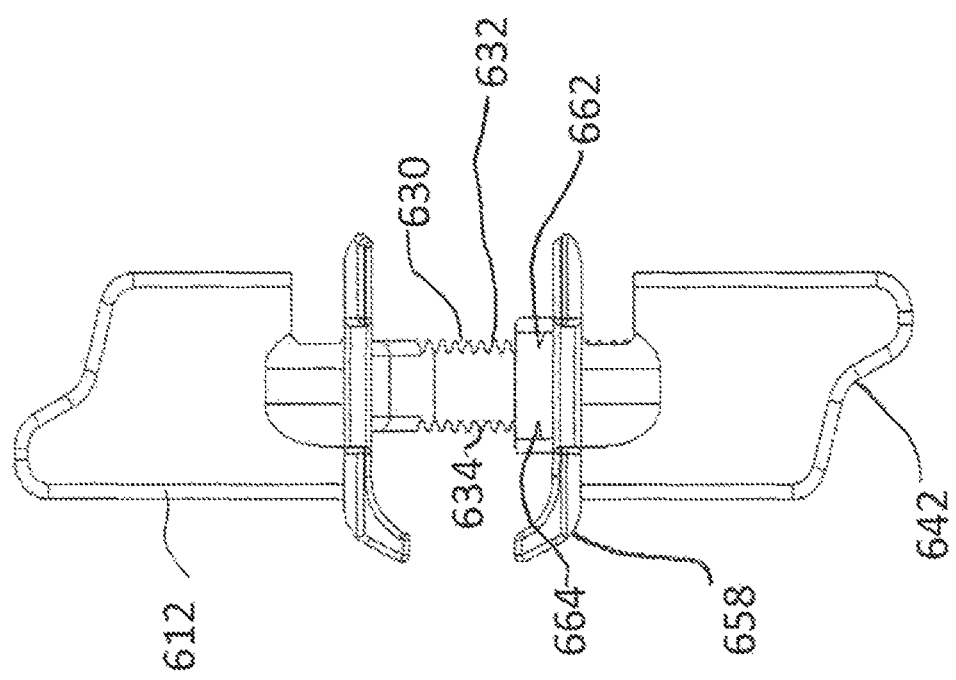
FIG. 22 is a lateral side elevational view of the expandable barrel assembly shown in FIG. 20, with the expandable barrel assembly in an expanded condition.

A receiver 660 extends laterally from proximal end 644 of lower barrel half 642. Receiver 660 is sized and adapted to receive post 630, such that post 630 is movable within receiver 660. Referring to FIG. 22, receiver 660 includes an internal tooth 662 that extends anteriorly into receiver 660 to engage ratchet teeth 632 on post 630. Similarly, receiver 660 includes an internal tooth 664 that extends posteriorly into receiver 660 to engage ratchet teeth 634 on post 630. Receiver teeth 662, 664 and ratchet teeth 632, 634 combine to form a ratchet assembly connecting upper barrel half 612 to lower barrel half 642 such that the ratchet assembly provides for relative vertical movement of upper barrel half 612 with respect to lower barrel half 642, but also restricts vertical movement without the use of distractor 700.

Figure 19:
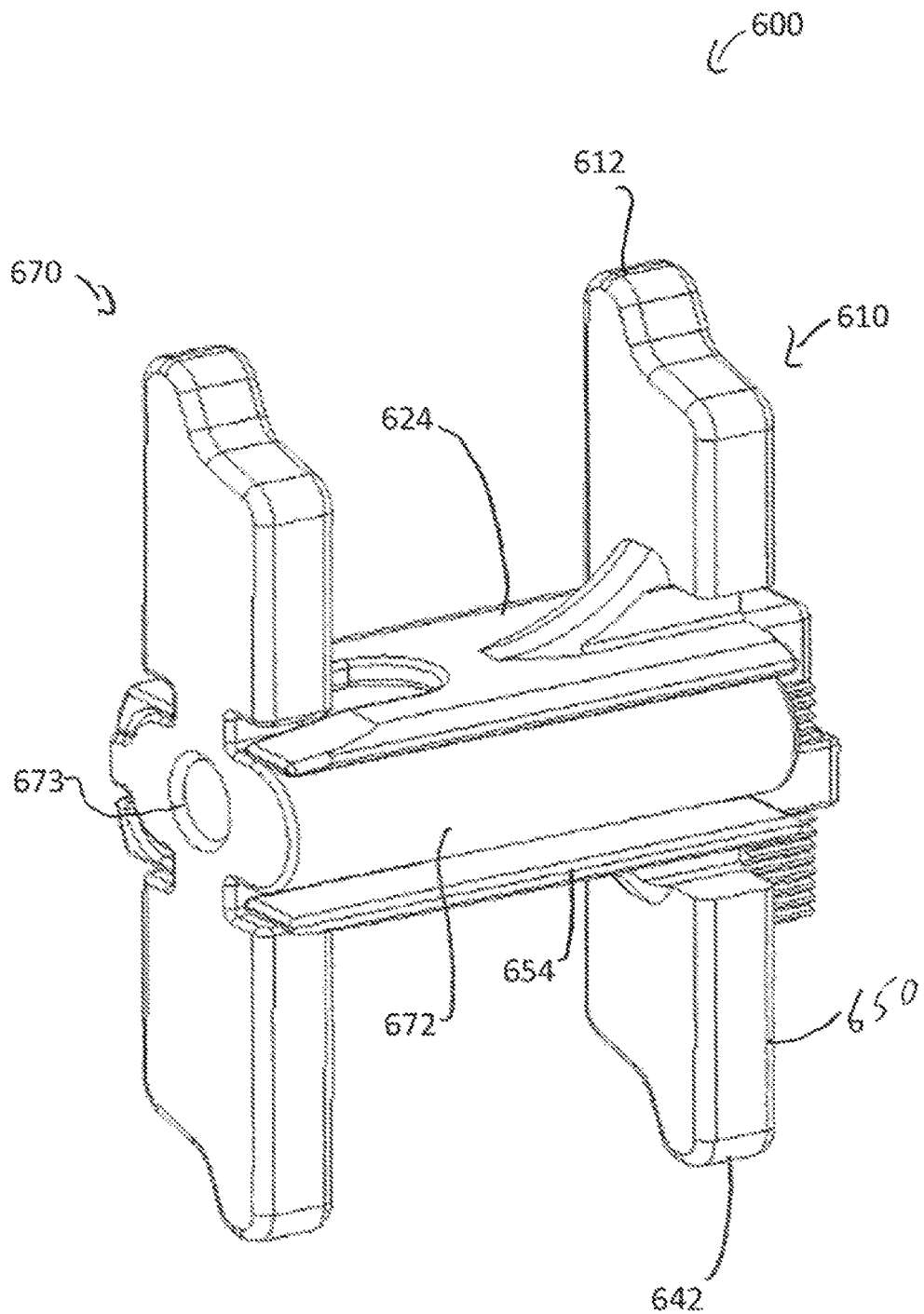
FIG. 19 is a front perspective view of an alternative embodiment of an expandable fixation system.
Figure 21:
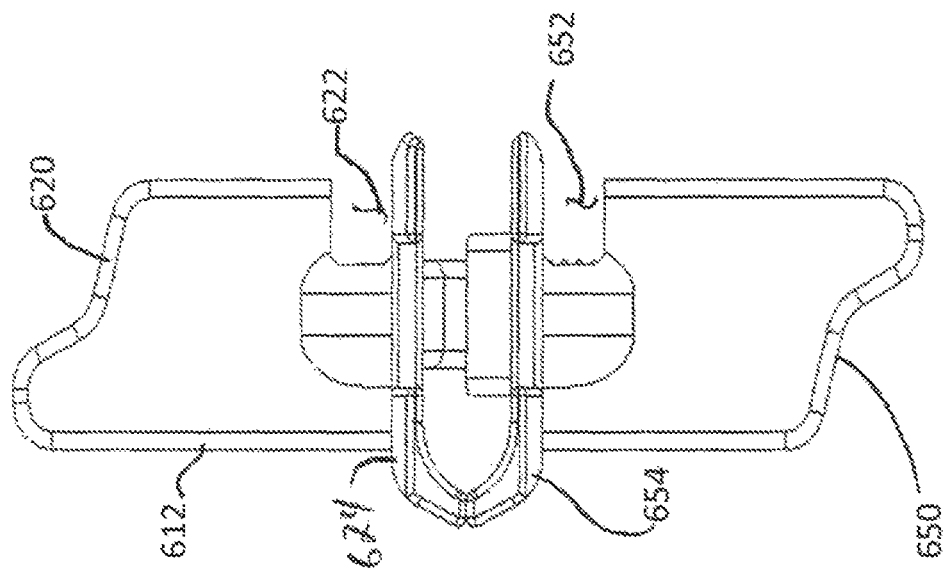
FIG. 21 is a lateral side elevational view of the expandable barrel assembly shown in FIG. 20, with the expandable barrel assembly in a compressed condition.
Figure 20:
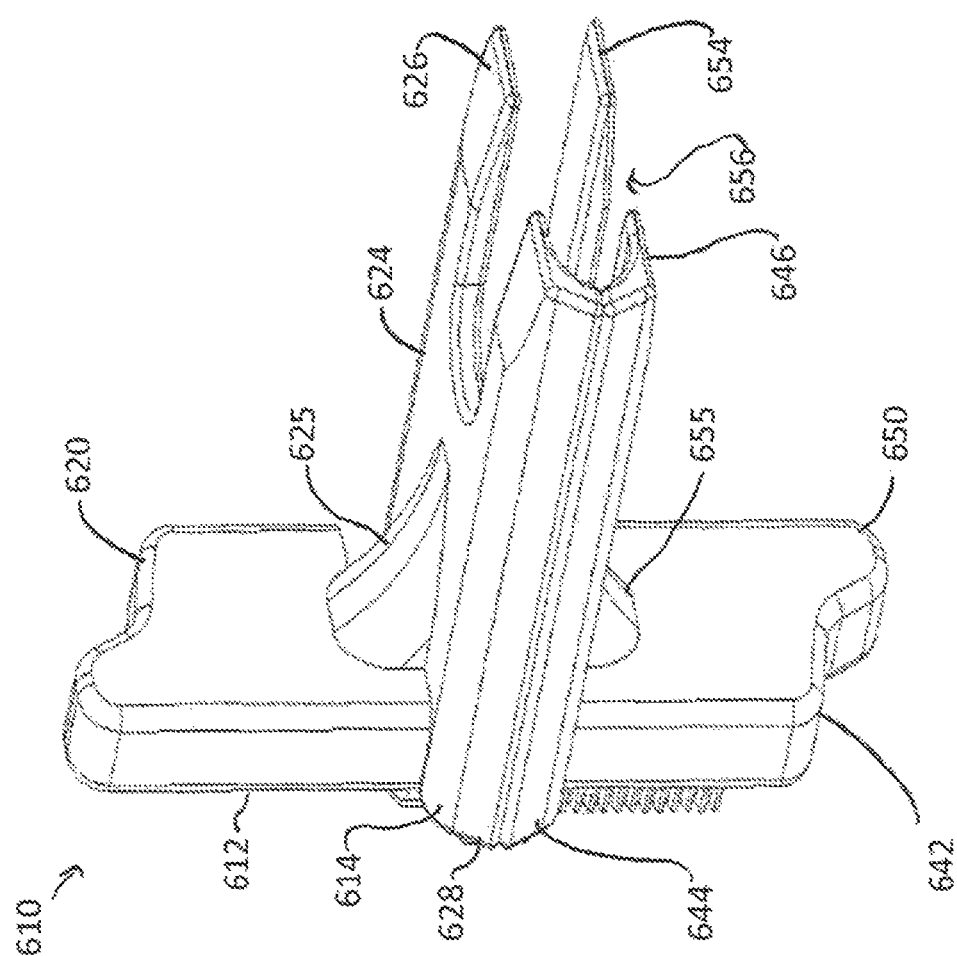
FIG. 20 is a rear perspective view of an expandable barrel assembly of the fixation system shown in FIG. 19.
Figure 23:
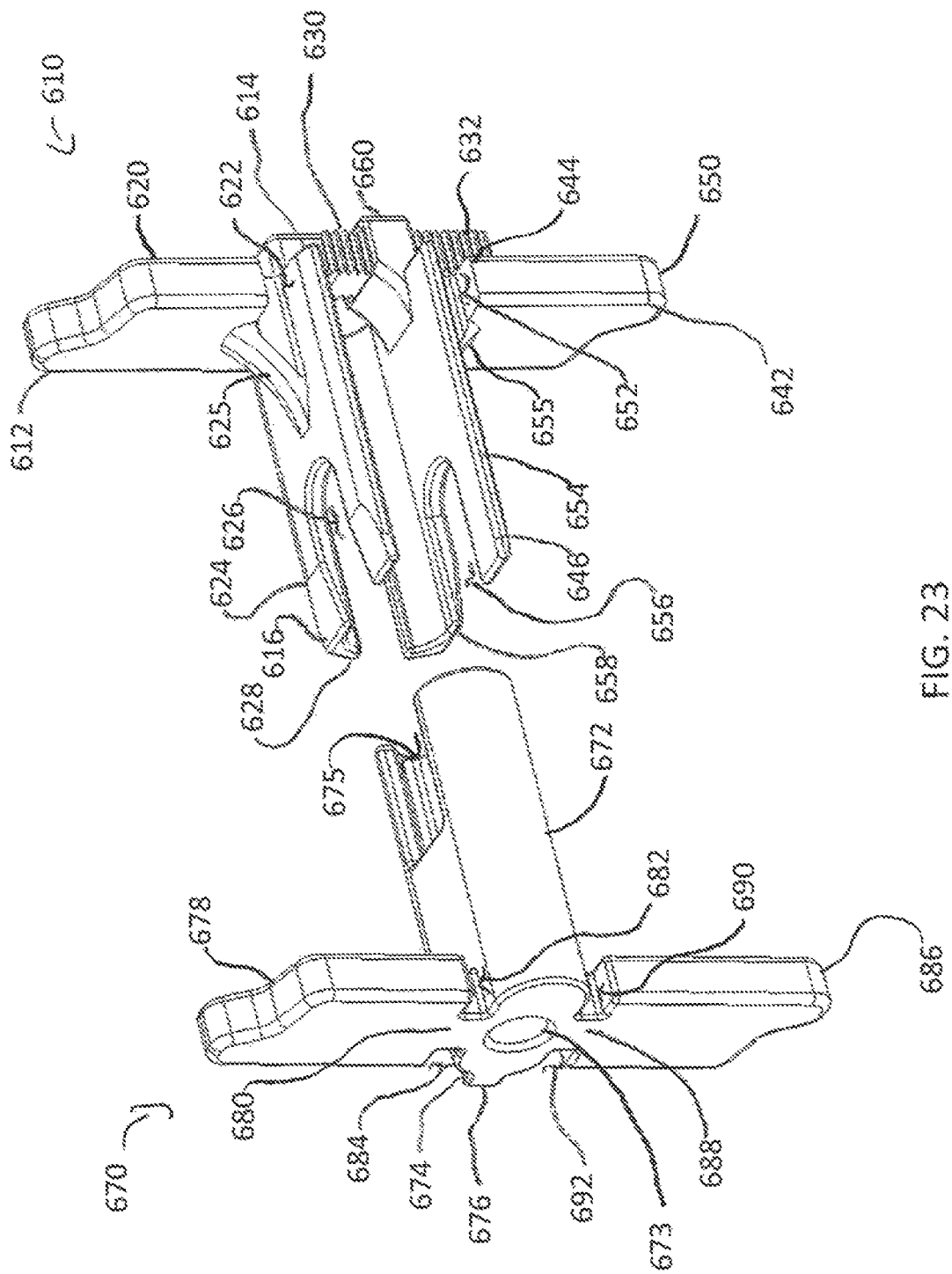
FIG. 23 is a front perspective view of the expandable fixation system shown in FIG. 19, with the expandable barrel assembly separated from the fixed barrel assembly.

Referring to FIGS. 19 and 23, fixed barrel assembly 670 has a body 672 that is sized to fit between upper barrel half 612 and lower barrel half 642 in one of an anterior-to-posterior direction and a lateral direction. Body 672 has an arcuate anterior side 674 that is adapted to engage first arcuate portion 628 on upper barrel half 612 and second arcuate portion 658 on lower barrel half 642. Anterior side 674 includes an anterior projection 676 that fits between first arcuate portion 628 and second arcuate portion 658 and acts as a key to guide fixed barrel assembly 670 into position between upper barrel half 612 and lower barrel half 642. Body 672 is hollow and includes a proximal opening 673 that is sized to allow for the insertion of graft material (not shown) after insertion of fixation assembly 600 into the patient. Body 672 also has a notch 675 formed at a distal end thereof. Notch 675 is sized to receive post 630 and receiver 660 when fixed barrel assembly 670 is inserted into expandable barrel assembly 610 from a lateral direction.

Fixed barrel assembly 670 further includes an upper plate 678 that extends upwardly from body 672. Upper plate 678 includes a plurality of medially extending spikes (not shown for clarity) that engage spinous process 50. Upper plate 678 also includes a first notched portion 680 that connects upper plate 678 to body 670. Notched portion 680 includes a posterior notch 682 and an anterior notch 684. Notches 682, 684 are sized to accept arm 624 on either side of U-shaped opening 626 such that notched portion 680 extends into U-shaped opening 626.

Fixed barrel assembly 670 also includes a lower plate 686 extending downwardly therefrom. Lower plate 686 includes a plurality of medially extending spikes (not shown for clarity) that engage spinous process 52. Lower plate 686 includes a second notched portion 688 that connects lower plate 686 to body 670. Notched portion 688 includes a posterior notch 690 and an anterior notch 692. Notches 690, 692 are sized to accept arm 654 on either side of U-shaped opening 656 such that notched portion 688 extends into U-shaped opening 656.

While, in an exemplary embodiment, fixation assembly 600 can be made from titanium, those skilled in the art will recognize that fixation assembly 600 can be made from other biocompatible materials, such as, for example, PEEK or allograft, with plates 620, 650, 678, 686 being constructed from titanium, for example.

Figure 24:
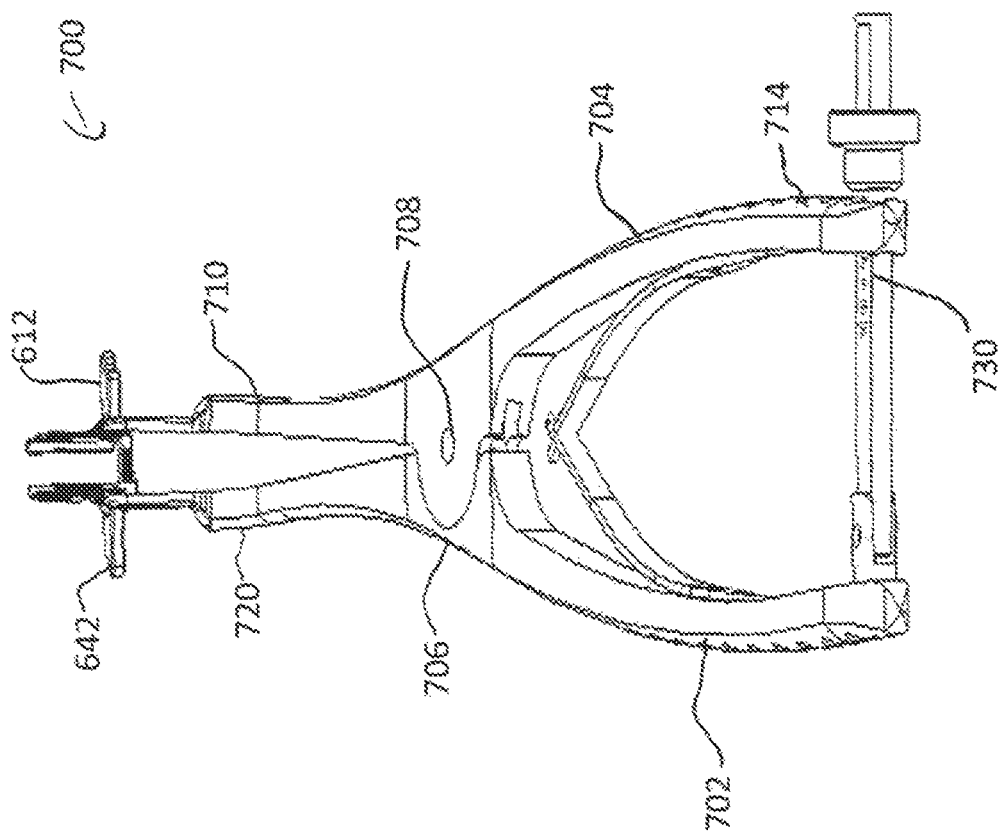
FIG. 24 is a perspective view of a distractor tool used to insert the expandable barrel assembly of the system shown in FIG. 19.
Figure 25:
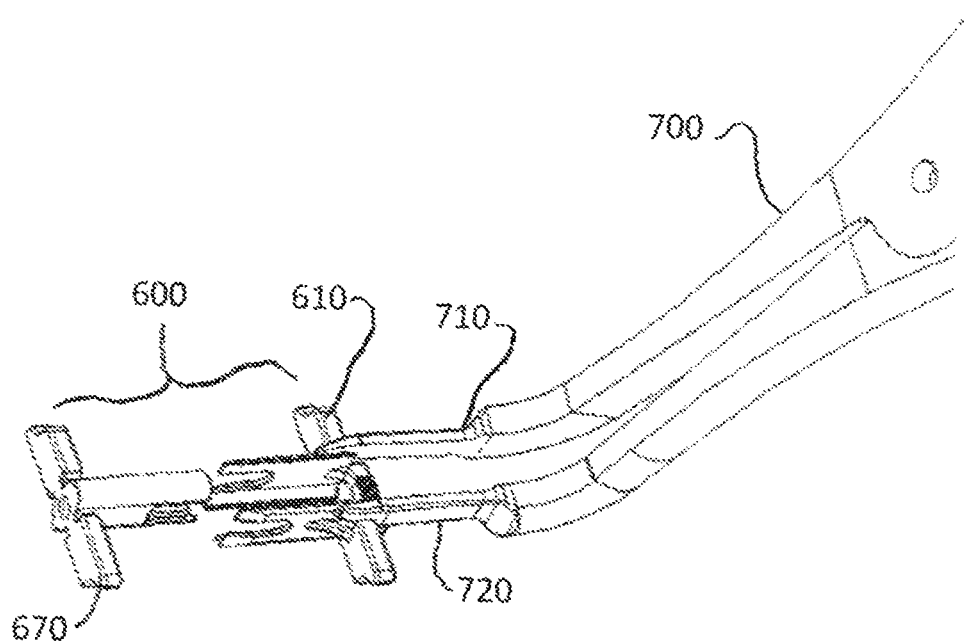
FIG. 25 is a perspective view of the distractor tool shown in FIG. 24 attached to the expandable barrel assembly of the expandable fixation system shown in FIG. 19.
Figure 26:
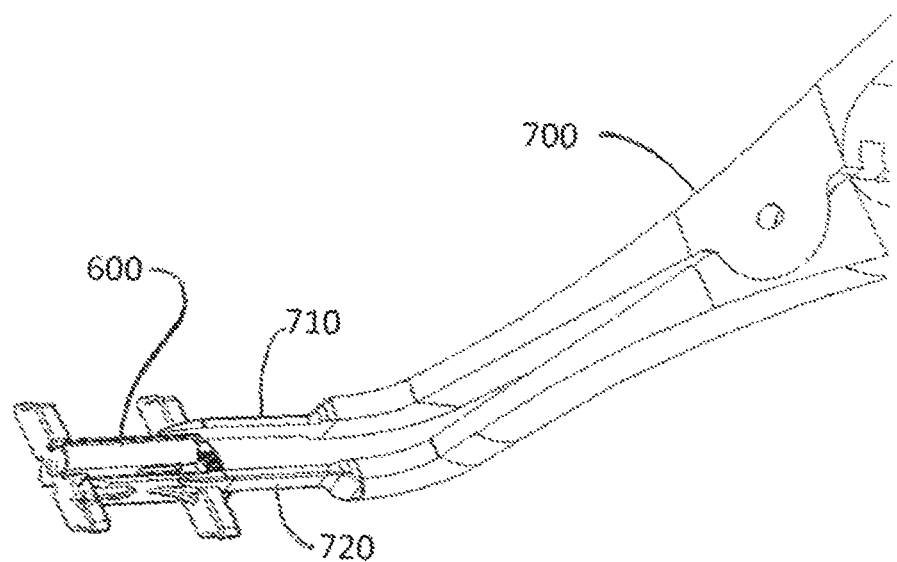
FIG. 26 is a perspective view of the distractor tool shown in FIG. 25, with the fixed barrel assembly inserted into the expandable barrel assembly.
Figure 27:
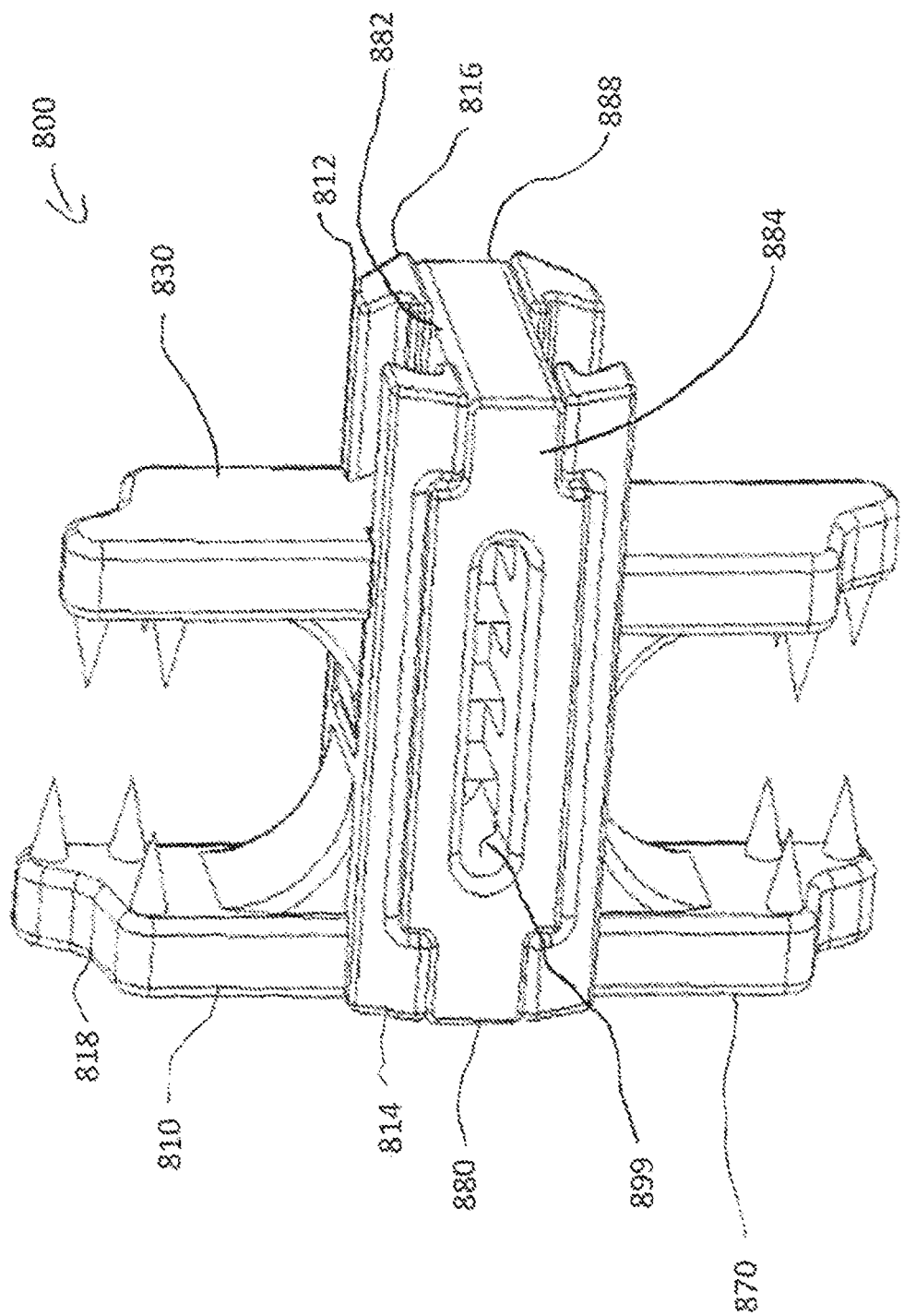
FIG. 27 is a perspective view of an alternative embodiment of an expandable assembly with an insert for an expandable fixation system in an assembled condition.

An exemplary distractor 700 is shown in FIGS. 24-26 and is used to manipulate expandable barrel assembly 610. Distractor 700 includes a first leg 702 and a second leg 704, attached to each other at a central portion 706 by a pivot pin 708.

First leg 702 includes a distal first finger 710 that is adapted to releasably engage upper barrel half 612. Second leg 704 includes a distal second finger 720 that is adapted to releasably engage lower barrel half 642 such that operation of distractor 700 vertically adjusts upper barrel half 612 with respect to lower barrel half 642 by moving upper barrel half 612 relative to lower barrel half 642 against the ratchet assembly. Embodiment, distractor 700 can be pre-packaged already attached to expandable barrel assembly 610.

First leg 702 also includes a first proximal handle end 714 and second leg 704 includes a second proximal handle end 724 that are gripped by a used. A distance gauge 730 is provided between first proximal handle end 714 and second proximal handle end 724 to indicate how far upper barrel half 612 is spaced from lower barrel half 642.

According to one embodiment, a method of installing fixation assembly 600 600, for example, at the site of spinous processes 50, 52, may include inserting first finger 710 into notch 622 in upper barrel assembly 612 and inserting second finger 720 into notch 652 in lower barrel assembly 642. Next, expandable barrel assembly 610 can be expanded to a desired height, as measured by distance gauge 730 on distractor 700. This measured value will determine the size of fixed barrel assembly 670.

Fixed barrel assembly 670 can be inserted into expandable barrel assembly 610 in one of two ways. For a lateral approach, fixed barrel assembly 670 can be inserted laterally from the distal end of expandable barrel assembly 610 and fit between upper barrel half 612 and lower barrel half 642.

For an alternative posterior-to-anterior surgical approach, fixed barrel assembly 670 can be inserted from the posterior side, such that anterior projection 676 is located between arcuate portion 628 of arm 624 on upper barrel half 612 and arcuate portion 658 of arm 654 on lower barrel half 642, which both act as a positive stop to prevent barrel 672 from being advanced too far anteriorly. Once located, the upper barrel half 612, lower barrel half 642, and fixed barrel half 670 can be compressed together against the spinous processes 50, 52. Fixed barrel half 670 can then be optionally back-filled with bone graft material.

The expansion of upper barrel half 612 and lower barrel half 642 is achieved using distractor 700. With the exemplary ratchet assembly, it is only possible to open upper barrel half 612 and lower barrel half 642 when distractor 700 is attached to fixation assembly 600. This will also prevent an expanded implant from collapsing should distractor 700 be removed prior to placement of a correctly sized fixed barrel assembly 670. Fixation assembly 600 will ratchet together as distractor 600 compresses upper barrel half 612 and lower barrel half 642 toward each other, locking the construct.

The expandable upper barrel half 612 and lower barrel half 642 allow fixation assembly 600 to be inserted at a minimum height and also provide interspinous distraction, off-loading the spikes on their respective plates 620, 650, 678, 686 and reducing the chances of breaking either spinous process 50, 52. Adjustable barrel assembly 610 is inserted at a collapsed height small enough to fit into the interspinous space between spinous processes 50, 52 without resistance (between about 4 mm and about 6 mm), and expand upper barrel half 612 away from lower barrel half 642.

Alternatively, the upper and lower halves 612, 642, respectively, do not need to be connected or locked in place. In such a design, distractor 700 would keep barrel halves 612, 642 open in the distracted/expanded state until fixed barrel assembly 670 is inserted. When distractor 700 is released, barrel halves 612, 642 settle on the barrel 672, which keeps the construct in the formerly expanded state. Undersizing of barrel 672 will also help prevent over distraction of the interspinous space, causing kyphosis.

An alternative embodiment of a spinous process fixation assembly 800 ("fixation assembly 800") is shown in FIGS. 27-38. Fixation assembly 800 allows for separate adjustment of fixation plates, depending upon the particular anatomy of spinous processes 50, 52 in a patient.

Figure 30:
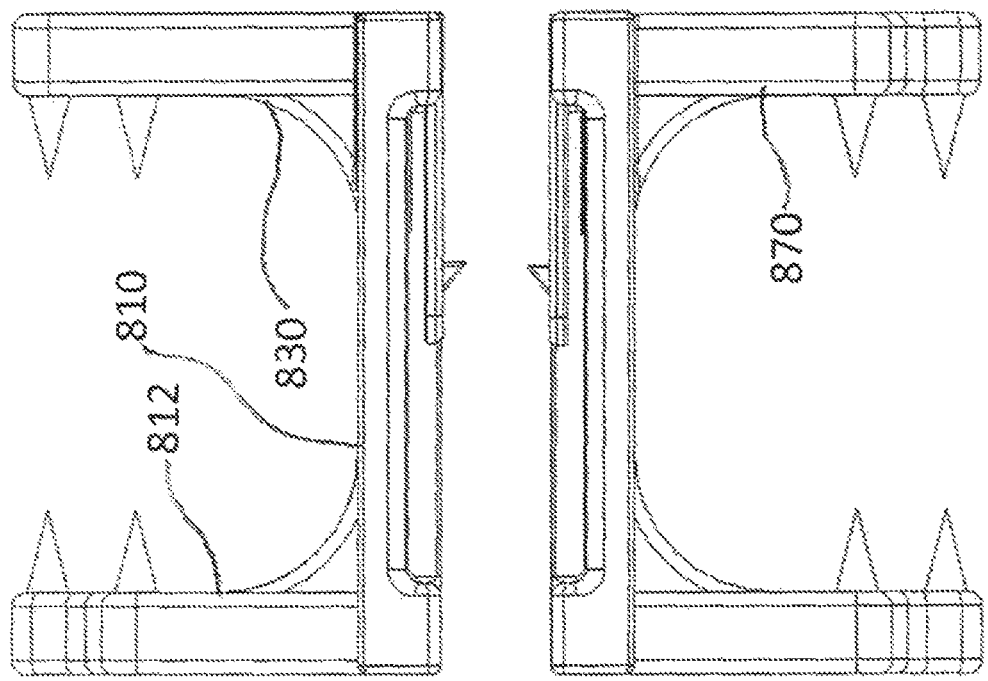
FIG. 30 is a side elevational view of the expandable assembly shown in FIG. 27, in a separated condition.
Figure 29:
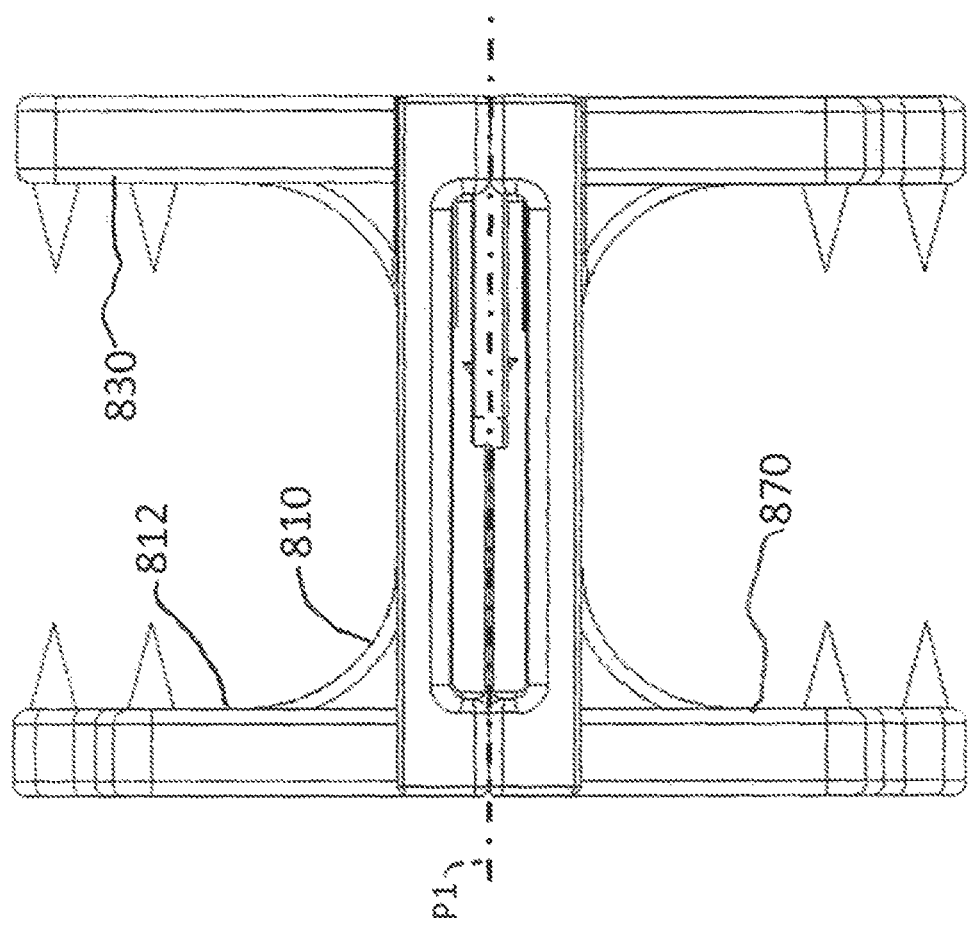
FIG. 29 is a side elevational view of the expandable assembly shown in FIG. 27, in an engaged condition.

Fixation assembly 800 includes an upper plate half 810, a lower plate half 870, and an insert 880 that is inserted in a posterior-to-anterior direction between upper plate half 810 and lower plate half 870. Upper plate half 810 and lower plate half 870 begin in a low-profile state, as shown in FIG. 29, that allows for insertion with an integrated holder/distractor (not shown) at a height of between about 4 mm and about 6 mm. Upper plate half 810 and lower plate half 870 can be separated from each other, as shown in FIG. 30, allowing for the selection of an appropriate sized insert 880 (shown in FIG. 31) to fit therebetween, forming fixation assembly 800, shown in FIG. 32.

Figure 32:
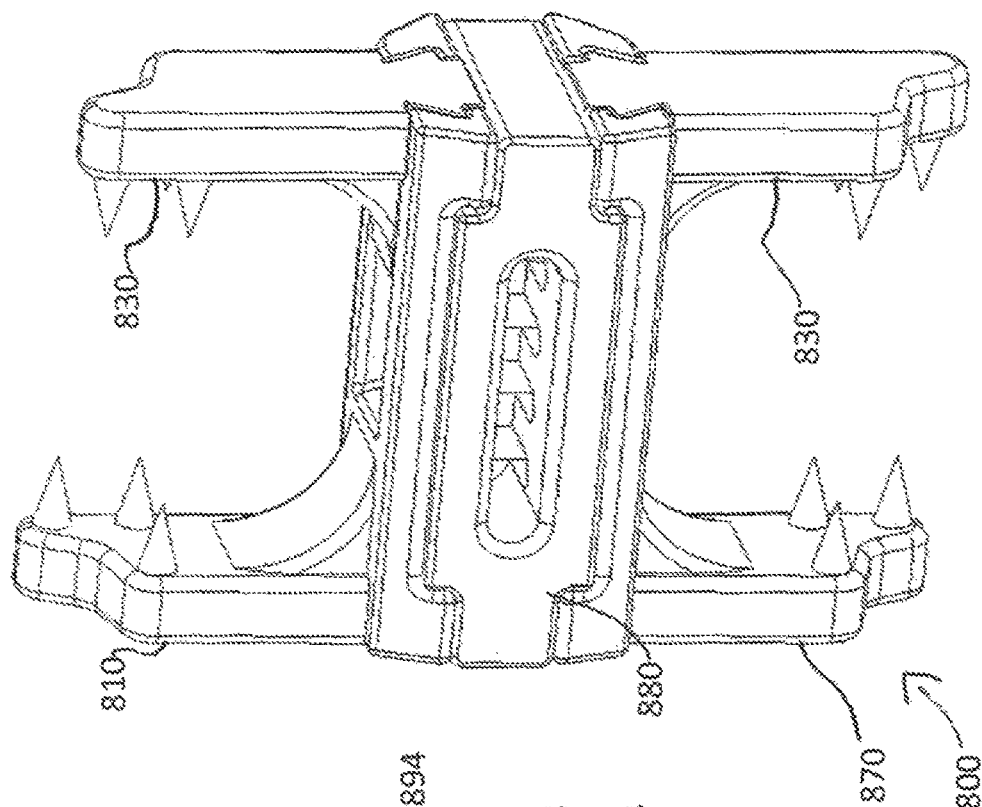
FIG. 32 is a perspective view of the expandable fixation system shown in FIG. 27, in an assembled condition, with upper and lower fixation plates in an open position.
Figure 34:
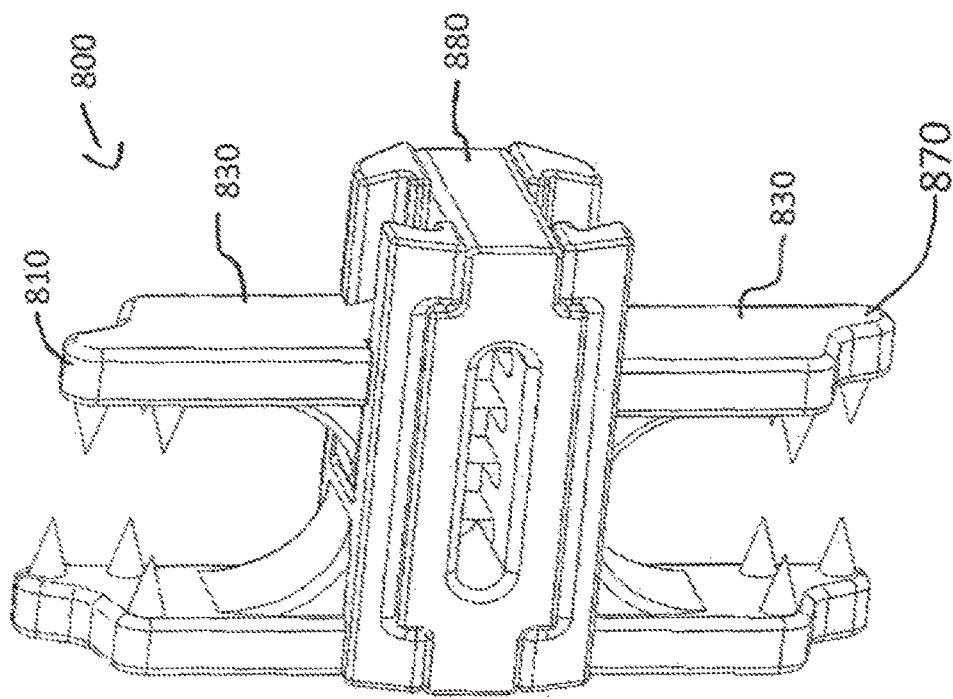
FIG. 34 is a perspective view of the expandable fixation system shown in FIG. 32, with both the upper fixation plate and the lower fixation plates in a compressed condition.
Figure 33:
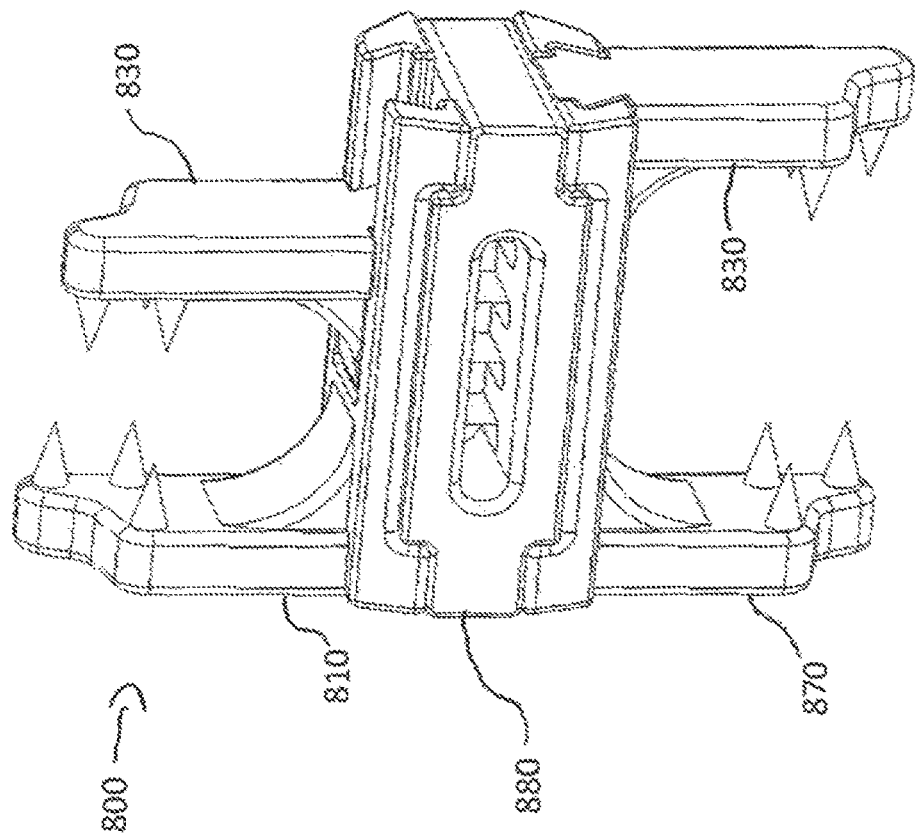
FIG. 33 is a perspective view of the expandable fixation system shown in FIG. 32, with the upper fixation plate in a compressed condition.
Figure 36:
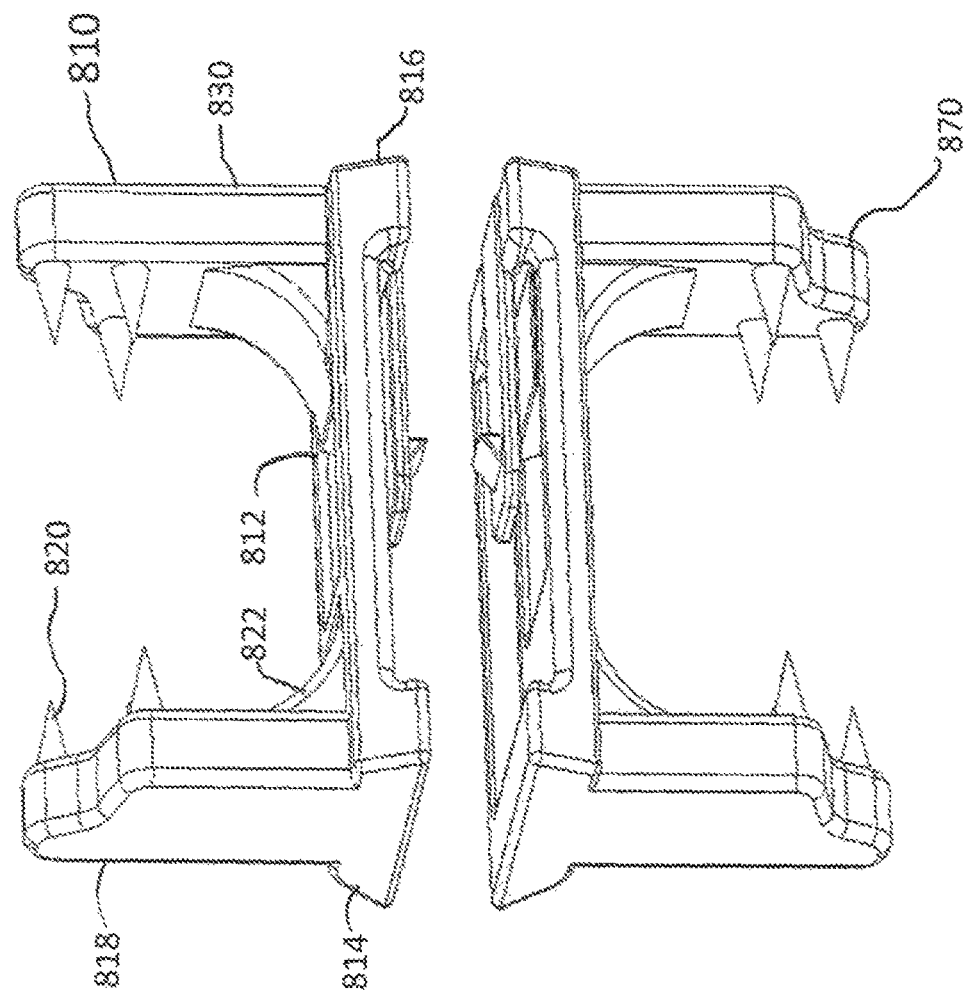
FIG. 36 is a perspective view of the expandable assembly shown in FIG. 27, a separated condition.
Figure 35:
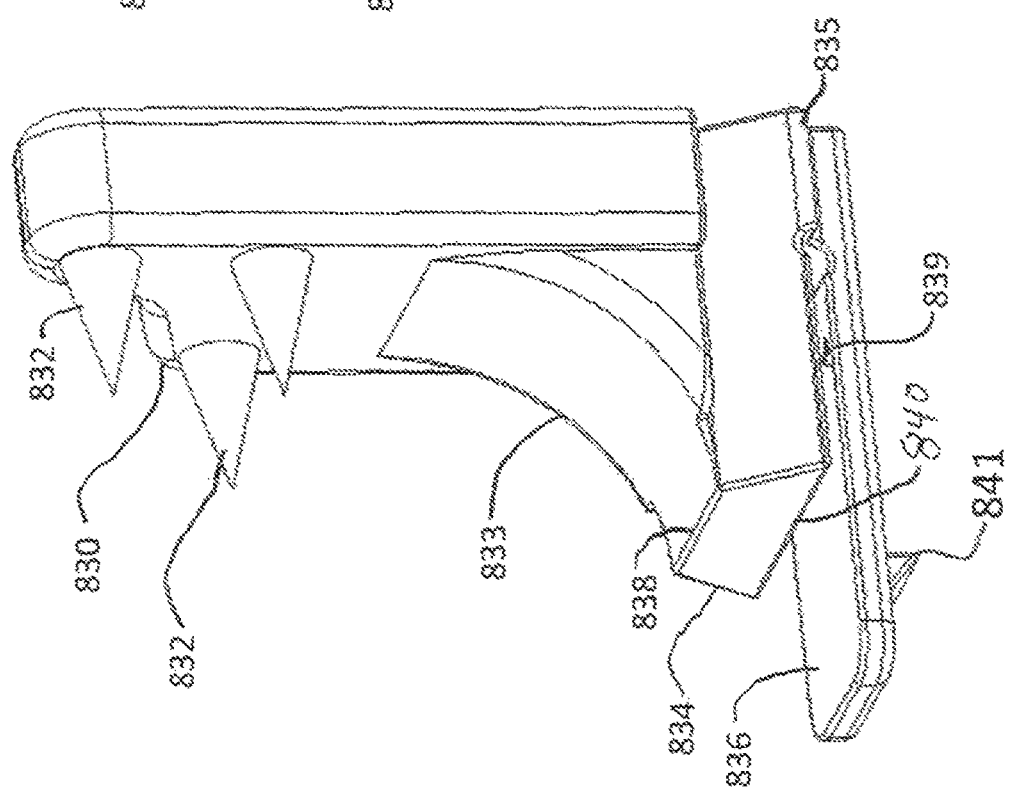
FIG. 35 is an enlarged perspective view of the upper fixation plate of the expandable fixation system shown in FIG. 27.

As shown in the progression of fixation assembly 800 from FIG. 32-FIG. 34, upper plate half 810 and lower plate half 870 can each have insertion plates that are spaced apart from each other; only upper plate half 810 has insertion plates compressed medially toward each other; and both upper plate half 810 and lower plate half 870 has insertion plates compressed medially toward each other, respectively. The ability to independently compress upper plate half 810 and lower plate half 870 with respect to each other allows for a superior fit for the patient's anatomy, particularly in cases where the superior spinous process 50 and inferior spinous process 52 are considerably different.

Upper plate half 810 includes a generally planar base 812 having a first and 814, and a second end 816, distal from first end 814. First end 814 includes a fixed plate 818 that extends upwardly therefrom. A plurality of spikes 820 extending medially inwardly from fixed plate 818. Spikes 820 are used to engage spinous process 50 (shown in FIG. 4). A gusset 822, located at the medial intersection of first end 814 and fixed plate 818, provides structural support for plate 818 relative to base 812.

Second end 816 includes a slidable plate 830 that is medially translatable toward fixed plate 818. Plate 830 is shown in detail in FIG. 38. Plate 830 includes a plurality of spikes 832 extending medially inward from slidable plate 830. Spikes 832 are used to engage an opposing side of spinous process 50 from fixed plate 818. Slidable plate 830 includes a sliding base 834, with a gusset 833, located at the medial intersection of plate 830 and sliding base 834, providing structural support for plate 830 relative to sliding base 834.

Base 834 has a generally dovetail or trapezoidally shaped cross-section, with a superior surface 838 at gusset 833 having a smaller length than an inferior surface 840, so that base 834 can slide a track in upper plate half base 812, as will be discussed herein.

Base 834 also includes a lateral spacer 835. An inferior tab 836 cantilevers medially from lateral spacer 835, forming a clevis-shaped opening 839 that allows for the biasing of inferior tab 836 in an upward direction as plate 830 is traversed medially. Tab 836 includes a tooth 841 extending downwardly therefrom to engage insert 880, allowing slidable plate 832 translate medially, but not laterally.

Figure 28:
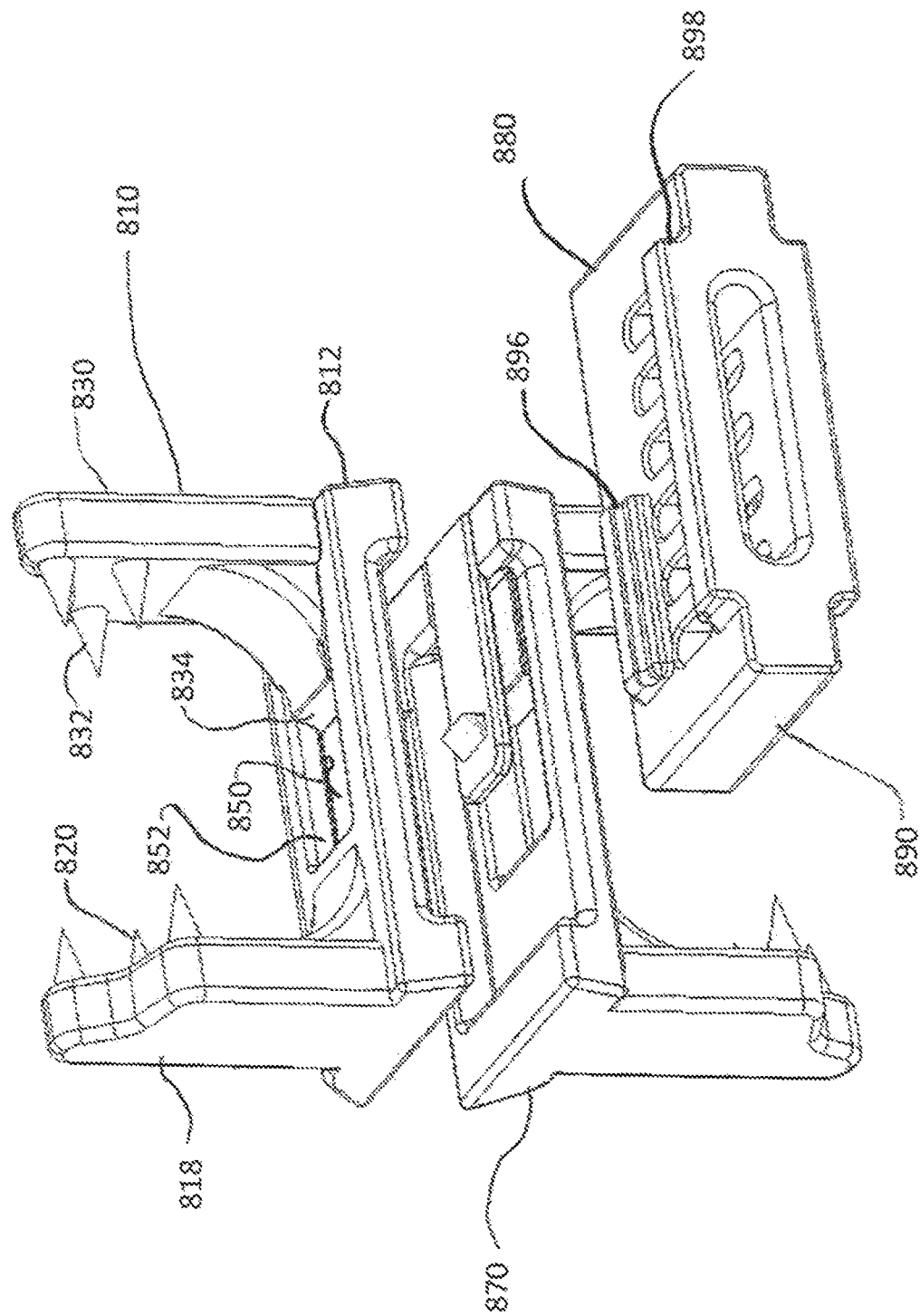
FIG. 28 is a perspective view of the expandable fixation system in a disassembled condition.
Figure 37:
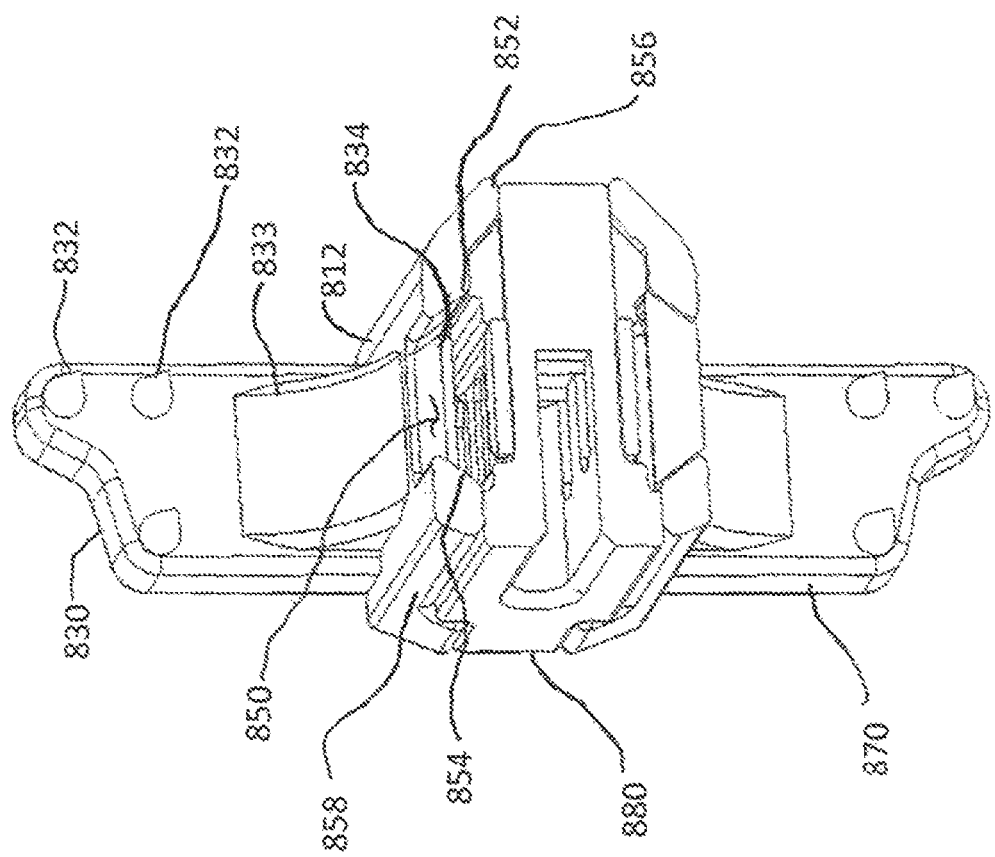
FIG. 37 is a sectional view of the expandable fixation system shown in FIG. 32.

As shown in FIGS. 28 and 37, base 812 includes a cavity 850, along which base 834 slides. Cavity 850 includes sloping anterior and posterior sides 852, 854, respectively, providing a mating engagement with dovetail or trapezoidally shaped base 834 to prevent base 834 of plate 830 from being able to separate superiorly from base 812. While fixation assembly 800 uses a dovetail connection as described above, those skilled in the art will recognize that other types of connections, such as, for example, a T-slot connection, can be used.

Base 812 includes an anterior side portion 856 that extends farther inferiorly than posterior side portion 858. Insert 880 is inserted from a posterior-to-anterior direction and the longer anterior side portion 856 act as a positive stop to prevent insert 880 from falling into the patient's spinal canal. Additionally, posterior side portion 858 at each of first end 814 and second end 816 extends farther inferiorly than a medial portion of posterior side portion 858, and also act as a positive stop to prevent insert 880 from traversing laterally with respect to upper plate half 810 and lower plate half 870.

Lower plate 870 is a mirror image of upper plate 810 across plane "P1" that extends orthogonally from the plane of the paper of FIG. 29, so the features of lower plate 870 need not be described in detail.

Figure 31:
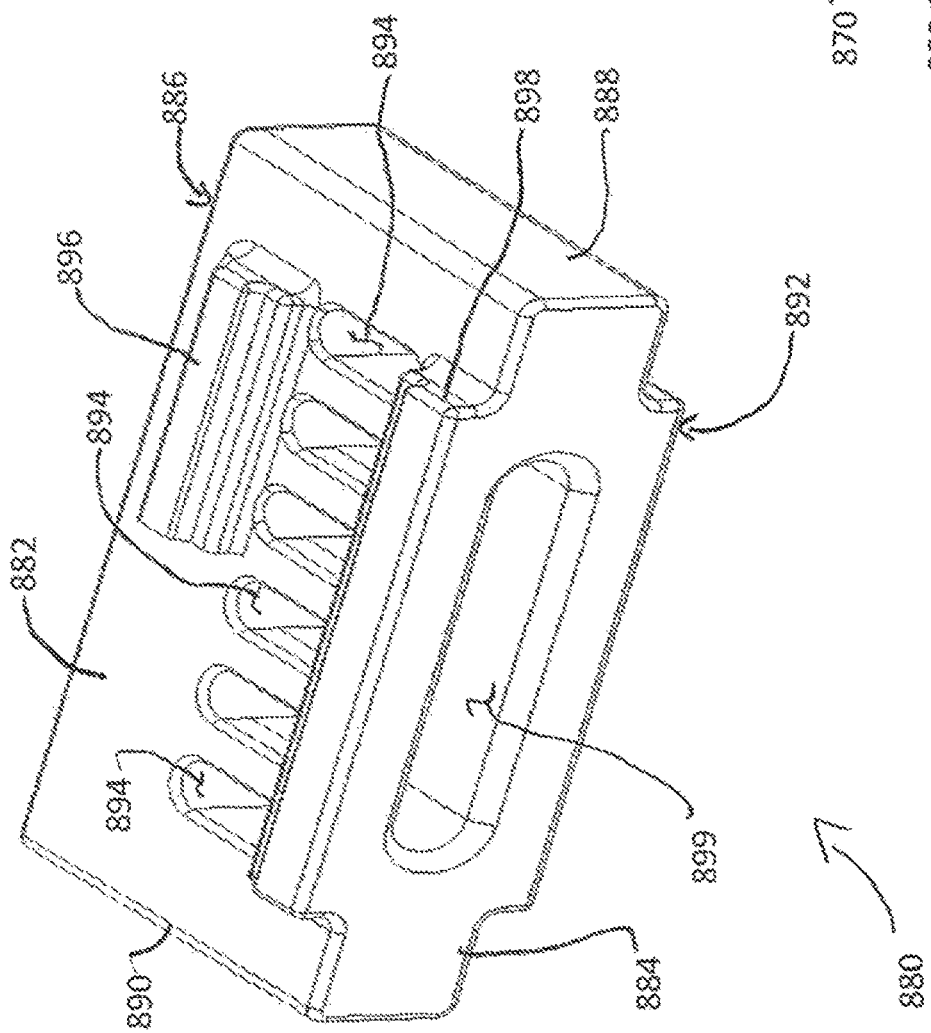
FIG. 31 is a perspective view of the insert shown in FIG. 27.
Figure 38:
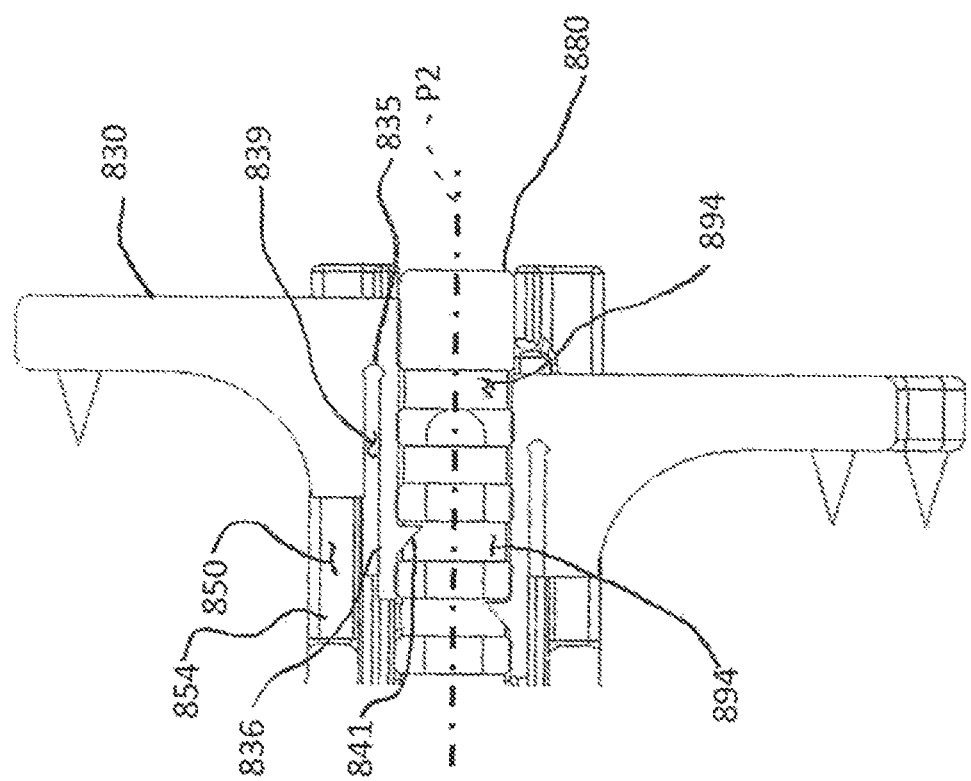
FIG. 38 is a sectional view of a spinous process engagement end of the expandable fixation system shown in FIG. 32.

Referring FIGS. 28, 31, and 38, insert 880 is a generally hollow parallelepiped shaped device having a top surface 882, a posterior surface 884, an anterior surface 886, and opposing lateral surfaces 888, 890. A bottom surface 892 is a mirror image of top surface 882 about plane "P2" extending orthogonally from the plane of the paper of FIG. 38, so the features of bottom surface 892 need not be described in detail. Insert 880 can be constructed from PEEK, titanium, allograft or other biocompatible material.

Top surface 882 includes a plurality of spaced openings 894 extending between lateral surfaces 888, 890 that are sized to allow tooth 841 to ratchet into as base 830 is traversed medially along cavity 850.

Top surface 882 also includes anterior and posterior rails 896, 898, respectively, that each extends in a medial-to-lateral direction. Rails 896, 898 support base 834, allowing tab 836 and tooth 841 to spring upward and over top surface 882, between openings 894 when plate 830 is compressed toward fixed plate 818.

Anterior rail 896 extends only about half the length of insert 880, while posterior rail 989 extends between first end 814 and second end 816 of upper plate half 810 such that, when insert 880 is inserted between upper plate half 810 and lower plate half 870, no gap is present between upper plate half 810 and insert 880, as well as between lower plate half 870 and insert 880.

Posterior surface 884 includes an opening 899 formed therein to allow the insertion of graft material into insert 880, if desired.

In the event that it is desired to remove insert 880 after implantation for replacement with a different insert having a different height, upper plate half 810 and lower face has 170 can be slightly distracted from each other, disengaging tooth 841, from the opening 894 into which it has been inserted, allowing insert 882 the posteriorly removed from fixation assembly 800.

Alternatively, although not shown, adjustable plates of fixation assembly 800 can be incorporated into fixation assembly 600 to allow for both vertical and lateral/medial adjustment of the assembly according to the particular patient anatomy.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A method of fixating adjacent spinous processes, said method comprising:
providing an expandable barrel assembly, wherein the expandable barrel assembly includes:
an upper barrel half, a lower barrel half, and an assembly connecting the upper barrel half to the lower barrel half, wherein the assembly is configured to move the upper barrel half with respect to the lower barrel half; and
a fixed barrel assembly having a body, an upper plate extending upwardly from the body, a lower plate extending downwardly from the body, the body sized to fit between the upper barrel half and the lower barrel half,
providing a distractor having a first arm and a second arm configured to be movable relative to the first arm, each arm having a finger insertable to a respective one of the upper and lower barrel halves to couple the distractor to the upper and lower barrel halves such that the upper barrel half is movable relative to the lower barrel half only when the distractor is coupled to the upper and lower barrel halves;
coupling the distractor to the upper and lower barrel halves;
attaching the expandable barrel assembly to the adjacent spinous processes; and
adjusting a distance between the upper barrel half and the lower barrel half with the assembly using the coupled distractor.

2. The method of claim 1, wherein the assembly comprises a tab extending downwardly from a proximal end of the upper barrel half, and wherein the assembly further comprises a receiver extending laterally from a proximal end of the lower barrel half, the receiver adapted to receive the tab, such that the tab is movable within the receiver.

3. The method of claim 2, wherein the upper barrel half comprises a first generally planar arm extending between the proximal end of the upper barrel half and a distal end of the upper barrel half and a first arcuate portion extending anteriorly downwardly from the first generally planar arm.

4. The method of claim 3, wherein the distal end of the upper barrel half has a first generally U-shaped opening in the first planar arm.

5. The method of claim 4, wherein the lower barrel half comprises a second generally planar arm extending between the proximal end of the lower barrel half and a distal end of the lower barrel half and a second arcuate portion extending anteriorly upwardly from the second generally planar arm such that, when the upper barrel half is vertically moved toward the lower barrel half, the first arcuate portion engages the second arcuate portion.

6. The method of claim 5, wherein the distal end of the lower barrel half has a second generally U-shaped opening in the second planar arm.

7. The method of claim 6, wherein the body of the fixed barrel assembly has an arcuate anterior side adapted to engage the first arcuate portion and the second arcuate portion.

8. The method of claim 7, wherein the fixed barrel assembly further comprises an upper plate extending upwardly therefrom and a lower plate extending downwardly therefrom.

9. The method of claim 8, wherein the upper plate comprises a first notched portion connecting the upper plate to the body, and wherein the lower plate comprises a second notched portion connecting the lower plate to the body.

10. The method of claim 9, wherein, when the expandable barrel assembly is advanced toward the fixed barrel assembly, the first notched portion extends into the first generally U-shaped opening and the second notched portion extends into the second generally U-shaped opening.

11. A method of fixating adjacent spinous processes, said method comprising:
providing an expandable spinal fixation system, wherein the expandable spinal fixation system includes:
an insert further including:
an expandable barrel assembly having an upper barrel half, a lower barrel half adjustably connected to the upper barrel half, and a fixed barrel assembly having a body sized to fit between the upper barrel half and the lower barrel half; and
an insertion tool having a first finger adapted to releasably engage the upper barrel half and a second finger adapted to releasably engage the lower barrel half such that operation of the insertion tool vertically adjusts the upper barrel half with respect to the lower barrel half and the upper barrel half is vertically adjustable relative to the lower barrel half only when the first and second fingers of the insertion tool are engaged with the upper and lower barrel halves,
coupling the first and second fingers of the insertion tool to the upper and lower barrel halves;
attaching the expandable spinal fixation system to the adjacent spinous processes; and
adjusting a distance between the upper barrel half and the lower barrel half using the coupled insertion tool.

12. The method of claim 11, wherein the upper barrel half comprises an upper plate extending upwardly therefrom and wherein the lower barrel half comprises a lower plate extending outwardly therefrom.

13. The method of claim 12, wherein the upper plate comprises a first notched portion connecting the upper plate to a proximal end of the upper barrel half and wherein the lower plate comprises a second notched portion connecting the lower plate to a proximal end of the lower barrel half.

14. The method of claim 13, wherein the first finger is releasably insertable into the first notched portion and wherein the second finger is releasably insertable into the second notched portion.

15. The method of claim 11, wherein the upper barrel half comprises a tab extending toward the lower barrel half, and wherein the lower barrel half comprises a receiver adapted to receive the tab.

16. The method of claim 15, wherein the tab and the receiver include a ratchet assembly.

17. The method of claim 16, wherein the insertion tool is configured to move the upper barrel half relative to the lower barrel half against the ratchet assembly.

* * * * *